(12) United States Patent
Reinherz et al.

(10) Patent No.: US 8,275,595 B2
(45) Date of Patent: Sep. 25, 2012

(54) COMPUTER-BASED METHODS OF DESIGNING MOLECULES

(75) Inventors: Ellis L. Reinherz, Lincoln, MA (US); Mikyung Kim, Boston, MA (US); Pedro Reche, Boston, MA (US); Jiahuai Wang, Belmont, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 366 days.

(21) Appl. No.: 10/486,278

(22) PCT Filed: Aug. 8, 2002

(86) PCT No.: PCT/US02/25263
§ 371 (c)(1),
(2), (4) Date: Jun. 23, 2004

(87) PCT Pub. No.: WO03/017032
PCT Pub. Date: Feb. 27, 2003

(65) Prior Publication Data
US 2005/0015232 A1    Jan. 20, 2005

(51) Int. Cl.
*G06G 7/58* (2006.01)
*G06G 7/48* (2006.01)
(52) U.S. Cl. .......................................... 703/12; 703/11
(58) Field of Classification Search .................. None
See application file for complete search history.

(56) References Cited

U.S. PATENT DOCUMENTS 5,608,037 A * 3/1997 Reinherz et al. ............... 530/350
5,935,579 A * 8/1999 Habeshaw et al. .......... 424/188.1
6,416,971 B1 * 7/2002 Reinherz et al. .............. 435/69.1

OTHER PUBLICATIONS

Ginalksi et al. "Practical Lessons from protein structure prediction", Nucleic ACids REsearch (2005) vol. 35, pp. 1874-1891.*
Bleicher et al. "Hit and lead generation: Beyond High-Throughput Screening" Nature Reviews: Drug Discovery (2003), vol. 2, pp. 369-378.*
Bohm et al. "Structure-Based design: molecular modelling merges with combinatorial chemistry", Current Opinion in Chemical Biology (2000) vol. 4, pp. 283-286.*
Rhodes et al. "Association and Colocalization of the KvB1 and KvB2 B-subunits with Kv1 a-subunits in Mammalian Brain K+ Channel Complexes" The Journal of Neuroscience (1997) vol. 17, pp. 8246-8258.*
Smith et al. "Expression and localization of epithelial sodium cannel in mammalian urinary bladder" The American Physiology Society (1998) pp. F91-F96.*
Ghiara et al., "Structure-based design of a constrained peptide mimic of the HIV-1 V3 loop neutralization site", J. Mol. Biol., 266 (1): 31-39 (1997).
Luo et al., "A molecular basis for functional peptide mimicry of a carbohydrate antigen", J. Biol. Chem., 275 (21): 16146-16154 (2000).
Murray et al., "Pro-Ligand: An approach to de novo molecular design. 6. Flexible fitting in the design of peptides", J. Computer-Aided Mol. Des., 9 (5):381-395 (1995).
Saphire et al., "Crystal structure of a neutralizing human IgG against HIV-1: A template for vaccine design", Science, 293 (5532): 1155-1159 (2001).

* cited by examiner

*Primary Examiner* — Eric S Dejong
(74) *Attorney, Agent, or Firm* — Fish & Richardson P.C.

(57) ABSTRACT

The invention features a method of generating an immunogenic compound with the ability to induce an immune response to a molecule produced by a pathogenic agent, e.g., a infectious agent or a tumor cell. Also included in the invention are an immunogenic compound generated by the method of the invention and a method of inducing an immune response in a mammal that involves administering the immunogenic compound to the mammal.

29 Claims, 9 Drawing Sheets

Fig. 2A atgggatgtcttgggaatcagctgcttatcgccatcttgcttttaagtgtctacgggatctattgt| actcaatatgtcac
agtcttttatggtgtaccagcttggaggaatgcgacaattcccctcttctgtgcaaccgagaatagggatacttggggaa
caactcagtgcctaccagataatggtgattattcagaattggcccttaacgttacagaaagctttgatgcctgggagaat
acagtcacagaacaggcaatagaggatgtatggcaactctttgagacctcaataaagccttgtgtaaaattatccccatt
atgcattactatgagatgcaataaaagtgagacagataaatggggattgacaaaatcattaacaacaacagcaccaacag
caccaacggcagcatcaaaaatagacatggtcaatgagactagttcttgtataactcatgataattgcacaggcttggaa
caagagcaaatgataggctgtaaattcaacatgacagggttaaaaagagacaagacaaggagtacaatgaaacttggta
ctctacagatttggtttgtgaacaagggaatagcactgataatgaaagtagatgctacatgaatcactgtaacacttcta
ttatccaagagtcttgtgacaagcattattgggatactattagatttaggtattgtgcacctccaggttatgctttgctt
agatgtaatgacacaaattattcaggctttatgcctaaatgttctaaggtggtggtctcttcatgcacaaggatgatgga
gacacagacttctacttggtttggctttaatggaactagagcagaaaatagaacttatatttactggcatggtagggata
ataggactataattagtttaaataagtattataatctaacaatgaaatgtagaagaccaggaaataagacagttttacca
gtcaccattatgtctggattggttttccactcacaaccaatcaatgataggccaaagcaggcatggtgttggtttggagg
aaattggaaggatgcaataaaagagatgaagcagaccattgtcaaacatcccaggtatactggaactaacaatactgata
aaatcaatttgacggctcctagaggaggagatccggaagttaccttcatgtggacaaattgcagaggagagttcctctac
tgtaaaatgaattggtttctaaattgggtagaagatagggatgtaactaaccagaggccaaaggaacggcatagaaggaa
ttacgtgccatgtcatattagacaaataatcaacacttggcataaagtaggcaaaaatgtttatttgcctccaagagagg
gagacctcacgtgtaactccacagtgaccagtctcatagcaaacatagattggactgatggaaaccaaactaatatcacc
atgagtgcagaggtggcagaactgtatcgattggaattgggagattataaattagtagagatcactccaattggcttggc
ccccacagatgtgaagaggtacactactggtggcacctcaagaaataaaagaggggtctttgtgctagggttcttgggtt
ttctcgcaacggcaggttctgcaatgggcgcggcgtcgttgacgctgaccgctcaatcccggactttattggctgggata
gtgcagcaacagcaacagctgttggacgtggtcaagagacaacaagaattgttgcgactgaccgtctggggaacaaagaa
cctccagactagggtcactgccatcgagaagtacttaaaggaccaggcgcagctgaatgcttggggatgtgcgtttagac
aagtctgccacactactgtaccatggccaaatgcaagtctaacaccagactggaacaatgatacttggcaagagtgggag
cgaaaggttgacttcttggaggaaaatataacagccctcctagaagaggcacaaattcaacaagagaagaacatgtatga
attacaaaagttgaatagctgggatgtgtttggcaattggtttgaccttgcttcttggataaagtatatacaatatggag
tttatatagttgtaggagtaatactgttaagaatagtgatctatatagtacaaatgctagctaagttaagacaggggtat
aggccagtgttctcttccccacccctcttatttccagcagacccatatccaacaggacccggcactgccaaccagagaagg
caaagaaggagacggtggagaaggcggtggcaacagctcctggccttggcagatagaatatattcatttcctgatccgcc
aactgatacgcctcttgacttggctattcagcaactgcagaaccttgctatcgagagcataccagatcctccaaccaata
ctccagaggctctctgcggccctacagagaattcgagaagtcctcaggactgaactgacctacctacaatatgggtggag
ctatttccaggaggcggtccaagtcggctggagatctgcgacagagactcttgcgggcgcgtggggagacttatggggaga
ctcttaggagaggtggaagatggatactcgcaatccctaggaggattagacaagggcttgagctcactctcttg

Fig. 2B

MGCLGNQLLIAILLLSVYGIYC| TQYVTVFYGVPAWRNATIPLFCATENRDTWG
TTQCLPDNGDYSELALNVTESFDAWENTVTEQAIEDVWQLFETSIKPCVKLSPLC
ITMRCNKSETDKWGLTKSLTTTAPTAPTAASKIDMVNETSSCITHDNCTGLEQEQ
MIGCKFNMTGLKRDKTKEYNETWYSTDLVCEQGNSTDNESRCYMNHCNTSIIQE
SCDKHYWDTIRFRYCAPPGYALLRCNDTNYSGFMPKCSKVVVSSCTRMMETQT
STWFGFNGTRAENRTYIYWHGRDNRTIISLNKYYNLTMKCRRPGNKTVLPVTIM
SGLVFHSQPINDRPKQAWCWFGGNWKDAIKEMKQTIVKHPRYTGTNNTDKINL
TAPRGGDPEVTFMWTNCRGEFLYCKMNWFLNWVEDRDVTNQRPKERHRRNYV
PCHIRQIINTWHKVGKNVYLPPREGDLTCNSTVTSLIANIDWTDGNQTNITMSAE
VAELYRLELGDYKLVEITPIGLAPTDVKRYTTGGTSRNKRGVFVLGFLGFLATAG
SAMGAASLTLTAQSRTLLAGIVQQQQQLLDVVKRQQELLRLTVWGTKNLQTRV
TAIEKYLKDQAQLNAWGCAFRQVCHTTVPWPNASLTPDWNNDTWQEWERKVD
FLEENITALLEEAQIQQEKNMYELQKLNSWDVFGNWFDLASWIKYIQYGVYIVV
GVILLRIVIYIVQMLAKLRQGYRPVFSSPPSYFQQTHIQQDPALPTREGKEGDGGE
GGGNSSWPWQIEYIHFLIRQLIRLLTWLFSNCRTLLSRAYQILQPILQRLSAALQRI
REVLRTELTYLQYGWSYFQEAVQVGWRSATETLAGAWGDLWETLRRGGRWIL
AIPRRIRQGLELTLL

Fig. 3A aggatgcaatgaagagagggctctgctgtgtgctgctgctgtgtggagcagtcttcgtttcgcccagcgctagc| actca
atatgtcacagtcttttatggtgtaccagcttggaggaatgcgacaattccctcttctgtgcaaccgagaatagggatacttgggg
aacaactcagtgcctaccagataatggtgattattcagaattggcccttaacgttacagaaagctttgatgcctgggagaat
acagtcacagaacaggcaatagaggatgtatggcaactctttgagacctcaataaagccttgtgtaaaattatccccatt
atgcattactatgagatgcaataaaagtgagacagataaatggggattgacaaaatcattaacaacaacagcaccaacag
caccaacggcagcatcaaaaatagacatggtcaatgagactagttcttgtataactcatgataattgcacaggcttggaa
caagagcaaatgataggctgtaaattcaacatgacagggttaaaaagagacaagacaaaggagtacaatgaaacttggta
ctctacagatttggtttgtgaacaagggaatagcactgataatgaaagtagatgctacatgaatcactgtaacacttcta
ttatccaagagtcttgtgacaagcattattgggatactattagatttaggtattgtgcacctccaggttatgctttgctt
agatgtaatgacacaaattattcaggctttatgcctaaatgttctaaggtggtggtctcttcatgcacaaggatgatgga
gacacagacttctacttggtttggctttaatggaactagagcagaaaatagaacttatatttactggcatggtagggata
ataggactataattagtttaaataagtattataatctaacaatgaaatgtagaagaccaggaaataagacagttttacca
gtcaccattatgtctggattggttttccactcacaaccaatcaatgataggccaaagcaggcatggtgttggtttggagg
aaattggaaggatgcaataaaagagatgaagcagaccattgtcaaacatcccaggtatactggaactaacaatactgata
aaatcaatttgacggctcctagaggaggagatccggaagttaccttcatgtggacaaattgcagaggagagttcctctac
tgtaaaatgaattggtttctaaattgggtagaagatagggatgtaactaaccagaggccaaaggaacggcatagaaggaa
ttacgtgccatgtcatattagacaaataatcaacacttggcataaagtaggcaaaaatgtttatttgcctccaagagagg
gagacctcacgtgtaactccacagtgaccagtctcatagcaaacatagattggactgatggaaaccaaactaatatcacc
atgagtgcagaggtggcagaactgtatcgattggaattgggagattataaattagtagagatcactccaattggcttggc
ccccacagatgtgaaggagtacactactggtggcacctcaagaaatgaaagaggggtctttgtgctagggttcttgggtt
ttctcgcaacggcaggttctgcaatgggcgcggcgtcgttgacgctgaccgctcaatcccggactttattggctgggata
gtgcagcaacagcaacagctgttggacgtggtcaagagacaacaagaattgttgcgactgaccgtctggggaacaaagaa
cctccagactagggtcactgccatcgagaagtacttaaaggaccaggcgcagctgaatgcttggggatgtgcgtttagac
aagtctgccacactactgtaccatggccaaatgcaagtctaacaccagactggaacaatgatacttggcaagagtgggag
cgaaaggttgacttcttggaggaaaatataacagccctcctagaagaggcacaaattcaacaagagaagaacatgtatga
attacaaaagttgaatagctgggatgtgtttggcaattggtttgaccttgcttcttggata

Fig. 3B

MDAMKRGLCCVLLLCGAVFVSPSAS| TVFYGVPAWRNATIPLFCATENRDT
WGTTQCLPDNGDYSELALNVTESFDAWENTVTEQAIEDVWQLFETSIKPCVKLS
PLCITMRCNKSETDKWGLTKSLTTTAPTAPTAASKIDMVNETSSCITHDNCTGLE
QEQMIGCKFNMTGLKRDKTKEYNETWYSTDLVCEQGNSTDNESRCYMNHCNTS
IIQESCDKHYWDTIRFRYCAPPGYALLRCNDTNYSGFMPKCSKVVVSSCTRMME
TQTSTWFGFNGTRAENRTYIYWHGRDNRTIISLNKYYNLTMKCRRPGNKTVLPV
TIMSGLVFHSQPINDRPKQAWCWFGGNWKDAIKEMKQTIVKHPRYTGTNNTDKI
NLTAPRGGDPEVTFMWTNCRGEFLYCKMNWFLNWVEDRDVTNQRPKERHRRN
YVPCHIRQIINTWHKVGKNVYLPPREGDLTCNSTVTSLIANIDWTDGNQTNITMS
AEVAELYRLELGDYKLVEITPIGLAPTDVKEYTTGGTSRNERGVFVLGFLGFLAT
AGSAMGAASLTLTAQSRTLLAGIVQQQQQLLDVVKRQQELLRLTVWGTKNLQT
RVTAIEKYLKDQAQLNAWGCAFRQVCHTTVPWPNASLTPDWNNDTWQEWERK
VDFLEENITALLEEAQIQQEKNMYELQKLNSWDVFGNWFDLASWI

Fig. 4A

MQYKLILNGKTLKGETTTEAVDAATAEKVFKQYANDNGVDGEWTYDDATKTF
TVTEGS*TWMEWEREIENYTGLIYTLIEESQNQQEKNEQDLLALDKWASLWNW
FDISNWLWYIK*MKQIEDKIEEILSKIYHIENEIARIKKLIGE

Fig. 4B

TWMEWEREIENYTGLIYTLIEESQNQQEKNEQDLLALDKWASLWNW
FDISNWLWYIK

Fig. 4C

SQNQQEKNEQDLL

COMPUTER-BASED METHODS OF DESIGNING MOLECULES

The work described in this application was supported in part by grant numbers AI43649 and AI50900 from the National Institute for Allergy and Immunological Diseases (NIAID). Thus the Government may have certain rights in the invention.

TECHNICAL FIELD

This invention relates to computer-based methods of designing molecules.

BACKGROUND

In view of the human and economic devastation inflicted by infectious diseases such as AIDS and malaria and malignant diseases such as breast and prostate cancer, it is imperative that immunogens be developed that can be used as prophylactic and/or therapeutic agents against them.

SUMMARY

The inventors have discovered a computer-based method for designing a compound useful for eliciting antibodies specific for a particular pathogenic agent. The method involves identifying the three-dimensional (3-D) structure of a segment of a pathogenic agent-derived, biological molecule (e.g., a protein) (designated herein as a pathogenic factor) that is likely to be an effective pathogenic agent-specific immunogen. Having obtained the 3-D structure of such a segment, a compound (e.g., a peptide) with essentially the same 3-D structure as the segment is synthesized and tested for its ability to elicit the production of antibodies in a mammalian host; such antibodies will preferably (though not necessarily) be protective from the pathogenic effect of a relevant pathogenic agent. A compound with the capacity to elicit the production of antibodies can then be manufactured.

More specifically, the invention features a computer-assisted method of generating an immunogen. The method requires the use of a programmed computer that includes a processor and an input device. The method involves: (a) providing a pathogenesis factor (PF), or a fragment of a PF, that contains a region with low polymorphism, the region being in an active conformation and being on an external surface of the PF; (b) obtaining data on the region in the active conformation, the data being useful for the determination of the three-dimensional structure of the region in the active conformation; (c) inputting to the input device the data; (d) determining, using the processor, the three-dimensional structure of the region in the active conformation; (e) designing a compound containing a domain that includes at least one epitope with the ability to induce the production in a mammal of an antibody that binds to the region in the active conformation; (f) producing the compound; and (g) determining whether the compound is an immunogen in a mammalian host. The PF can be a component, or an altered form of a component, of an infectious microorganism. In addition, the antibody that binds to the region in the active conformation can be an antibody that binds to a plurality of (e.g., two, three, four, five, six, seven, eight, nine, ten, 15, 20, 30, 40, 50, 60, 70, 80, 90, 100, 150, 200, 300, 500, 750, 1000, 1,500, 2000, 3,000, 5,000, 10,000, 20,000, 30,000, or all) strains (or isolates) of the infectious microorganism. The infectious microorganism can be a microorganism that replicates inside a cell.

It can be a virus, e.g., a retrovirus such as simian immunodeficiency virus (SIV) or human immunodeficiency virus (HIV). The microorganism can also be a protozoan parasite, e.g., malarial protozoan parasite, and the PF can be, for example, merozoite surface protein-1 (MSP-1), ring-infected erythrocyte surface antigen (RESA), *Plasmodium falciparum* erythrocyte membrane protein-1 (PfEMP-1), *Plasmodium falciparum* 332 antigen (pf332), Rosettin, merozoite surface protein-2 (MSP-2), serine stretch protein (SERP), glutamate-rich protein (GLURP), apical membrane antigen-1 (AMA-1), or histidine-rich protein-2 (HRP-2). Alternatively the microorganism can be a bacterium such as any of those listed herein. The PF, or a wild-type form of the PF, can mediate entry of the microorganism into a cell. Such a cell can be a CD4+ cell such as a T cell or a monocyte or a macrophage. The cell can also be, for example, an erythrocyte. The PF can be: (a) a naturally occurring polypeptide; (b) an altered form of a naturally occurring polypeptide; or (c) a molecular complex comprising two or more subunits, each subunit being either of (a) or (b). The PF can include a complex of retroviral envelope glycoproteins or recombinant forms of such proteins, e.g., it can contain three recombinant SIV gp140 polypeptides. The PF can be a component, or an altered form of a component, of a cancer cell, e.g., prostate-specific membrane antigen (PSMA) or any other tumor cell surface molecule. The PF can be provided in a crystalline form and the data can be a criteria data set that includes three-dimensional atomic coordinates.

The invention also includes a process of manufacturing a compound. The process involves: carrying out the above-described computer-assisted method of generating an immunogen; and, after determining that the compound is an immunogen, manufacturing the compound.

Another aspect of the invention is a method of testing a compound for prophylactic activity. The method involves administering a compound manufactured by the above-described method of manufacturing a compound to a mammal and testing for the presence in the mammal of antibodies that inhibit the pathogenicity of a pathogenic agent of which the PF is (a) a component or (b) an altered form of a component. In this method, the presence in the mammal of antibodies that inhibit the pathogenicity of the pathogenic agent is an indication that the compound has prophylactic activity against the pathogenic agent.

Another aspect of the invention is a compound manufactured by the above-described process of manufacturing a compound. The invention provides a method of inducing an immune response in a mammal. The method involves administering the above-described compound of the invention to the mammal. The compound can be administered to the mammal parenterally, intranasally, transcutaneously, or by any other route recited herein. The immune response can be a protective immune response and, as such, is preferably protective against a plurality of (e.g., two, three, four, five, six, seven, eight, nine, ten, 15, 20, 30, 40, 50, 60, 70, 80, 90, 100, 150, 200, 300, 500, 750, 1000, 1,500, 2000, 3,000, 5,000, 10,000, 20,000, 30,000, or all) strains (or isolates) of the infectious microorganism.

As used herein, "immunogenic" means capable of eliciting a functional immune response in a B precursor cell. As used herein, a B precursor cell is a B lymphocyte that, subsequent to activation, can produce antibody molecules. Activation of a B precursor cell can be, without limitation, by recognition of an antigen by an antigen specific immunoglobulin receptor on the B precursor cell. Thus, a B precursor cell can be a "virgin" B lymphocyte that has never previously been activated or a "memory" B lymphocyte that has previously been activated or the progeny of such a B lymphocyte.

As used herein, "antigenic" means capable of being recognized by an effector B lymphocyte or an antibody molecule. Thus, a substance is antigenic if it is recognized by an antigen specific receptor on, for example, a B lymphocyte producing antibody molecules or by an antibody molecule physically unassociated with a B lymphocyte.

"Polypeptide" and "protein" are used interchangeably and mean any peptide-linked chain of amino acids, regardless of length or post-translational modification.

As used herein, an expression control sequence that is "operably linked" to a coding sequence is incorporated into a genetic construct so it effectively controls expression of the coding sequence.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., designing efficacious immunogens, will be apparent from the following description, from the drawings and from the claims.

DESCRIPTION OF DRAWINGS

FIG. 2A: is a depiction of the nucleotide sequence (SEQ ID NO:1) of cDNA encoding simian immunodeficiency virus (SIV) strain Mac23HpJ5 gp160. The 3' end of the leader sequence is indicated by a vertical line.

FIG. 2B is a depiction of the amino acid sequence (SEQ ID NO:2) of SIV Mac23HpJ5 gp160. The cleavage site of the N-terminal signal sequence is indicated by a vertical line.

FIG. 3A is a depiction of the nucleotide sequence (SEQ ID NO:3) of cDNA encoding recombinant SIV Mac23HpJ5 gp140. The 3' end of the heterologous tissue plasminogen activator (tpA) leader sequence is indicated by a vertical line.

FIG. 3B is a depiction of the amino acid sequence (SEQ ID NO:4) of recombinant SIV Mac23HpJ5 gp140. The cleavage site of the heterologous tpA N-terminal signal sequence is indicated by a vertical line.

FIG. 4A is a depiction of the amino acid sequence (SEQ ID NO:15) of the GCG2 fusion protein.

FIG. 4B is a depiction of the amino acid sequence (SEQ ID NO:16) of the HIV-1 gp41 C-terminal ectodomain segment included in the GCG2 fusion protein.

FIG. 4C is a depiction of the amino acid sequence (SEQ ID NO:17) included in SEQ ID NO:16 that corresponds to a C-domain sequence in HIV-1 gp41 (having in the consensus sequence shown in the "ALL" chart in FIG. 1 the amino acid sequence SEQ ID NO:14) that, on account of its low polymorphism and predicted location on the surface of gp41 in its trimeric, prefusion state, is considered a promising candidate for immunogen development.

FIG. 5 is a photograph of a Coomassie blue-stained sodium dodecyl sulfate polyacrylamide gel electrophoresis (SDS-PAGE) gel of proteins immunoprecipitated by GammaBind Plus™ beads (Amersham Biosciences, Piscataway, N.J.) coated with the 2F5 monoclonal antibody (mAb) ("2F5 beads") or the 4E10 mAb ("4E10 beads"), both specific for HIV-1 gp41, that had been incubated with ("+") or without ("–") purified GCG2 fusion protein for 4 hours at 4° C. The right lane of the gel ("+") contained purified GCG2 protein. The positions of molecular weight markers are shown by the numbers to the right of the photograph; the numbers are the molecular weights (kDa×$10^{-3}$) of the markers.

DETAILED DESCRIPTION

Figure 1A:
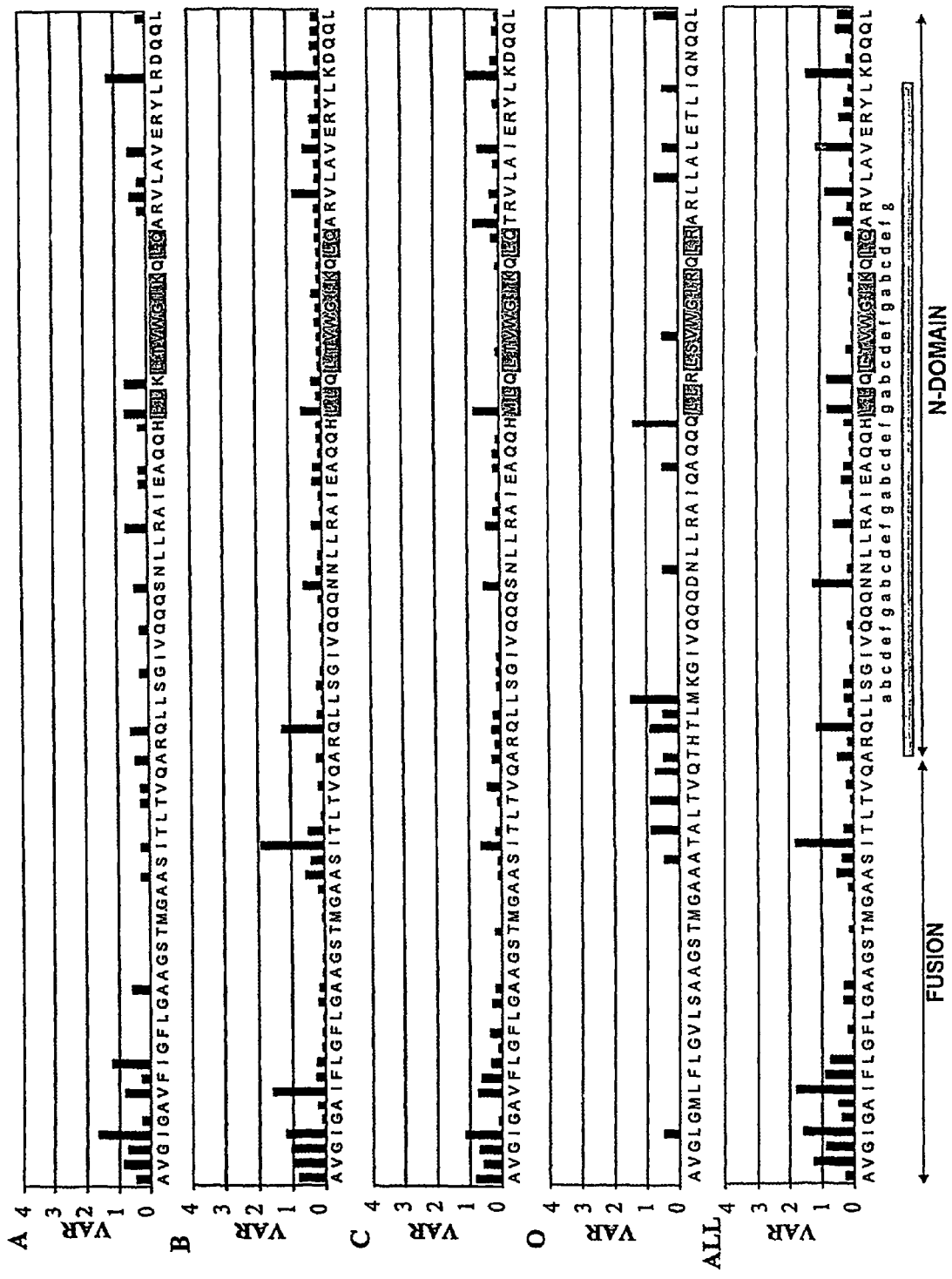
FIGS. 1A and 1B are bar charts showing the amino acid sequence variability of each amino acid of the gp41 ectodomain from HIV-1. Sequence variability ("VAR") at each amino acid sequence position is represented by the Shannon entropy (H) and gp41 ectodomain positions are indicated under the bar charts with the consensus amino acid residue at that position. H values and consensus amino acid residues were derived from multiple sequence alignments of gp41 isolates from HIV-1 clades A ("A") (SEQ ID NO:18), B ("B") (SEQ ID NO:19), C ("C") (SEQ ID NO:20), O ("O") (SEQ ID NO:21), and all isolates ("ALL") (SEQ ID NO:22), regardless of clade. The consensus amino acid residues were obtained at a 50% threshold (i.e., the indicated residue or residue type was present in at least 50% of the sequences analyzed). Upper case letters represent the relevant consensus amino acid residues. Lower case letters represent the following amino acid types: "o", amino acids with alcohol side chains (i.e., S or T); "." (dot), any amino acid; "c", amino acids with charged side chains (i.e., D, E, H, K, or R); "–", amino acids with negatively charged side chains (i.e., D or E); "p", amino acids with polar side chains (i.e., C, D, E, H, K, N, Q, R, S, or T); "+", amino acids with positively charged side chains (i.e., H, K, or R); "s", amino acids with small side chains (i.e., A, C, D, G, N, P, S, T, or V); and "u", amino acids with very small side chains (A, G, or S). Additional features shown are as follows: residues indicated by filled black boxes are cysteines that are believed to be engaged in a disulfide bridge; asparagine (N) residues framed by an open box are potential N-glycosylation sites; the boxed LDKWAS sequence (SEQ ID N0:5) is the target epitope of the 2F5 monoclonal antibody [Muster et al. (1993) J. Virol. 67(11); 6642-6647]; gray shaded residues in the N-domain form the lining of a hydrophobic cavity (observed in the x-ray crystallographically derived structure of the gp41 trimeric core [Chan et al. (1997) Cell 89(2)263-273]) which is occupied by residues of the C-domain (also shaded in gray). Underlined sequences in the loop and C domains of the ALL bar chart are sequences that are potential targets for immunogen development by the method of the invention. The various regions of gp41 (fusion peptide, N-domain, loop and C-domain) are indicated under the ALL bar chart. Additional 3-D structural information is provided under the ALL bar chart. Thus, helical regions observed in the previously described x-ray crystallographically derived structures of the trimeric gp41 core [Weissenhorn et al. (1997) Nature 387(6632):426-430; Chan et al. (1997) supra] are indicated by a filled cylinder. Secondary structure predictions, and a model of the full length gp41 [Caffrey (2001) Biochim Biophys. Acta 1536:116-122], indicate that the span of the helical regions is longer; this longer span of the helical regions is shown by an extended empty cylinder. The "a" to "g" letters under the consensus amino acids of the "ALL" bar chart mark the residues constituting the heptad repeats of the N- and C-domain helices. Interestingly, "a" and "d" residues of a given N-domain heptad repeat interact with "a" and "d" residues, respectively, of a neighboring N-domain heptad in the trimeric gp41 core structure, and residues "e" and "g" of a given C-domain heptad interact with "a" and "d" residues, respectively, of a neighboring C-domain hepad in the trimeric gp41 core structure [Chan et al. (1997) supra].

Various aspects of the invention are described below.

Computer Hardware and Software

The invention can be implemented in computer hardware or software, or a combination of both. However, the invention is preferably implemented in one or more computer programs executing on one or more programmable computers, each containing a processor and at least one input device. The computers will preferably also contain a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing an immunogenic compound can minimally involve:

(a) inputting into an input device, e.g., through a keyboard, a diskette, or a tape, data that can be used to determine the 3-D structure of a PF region having low polymorphism, e.g., a criteria data set containing 3-D atomic co-ordinates of the region; and (b) determining, using a processor, the 3-D structure of the region.

The method can involve the additional step of outputting to an output device a model of the 3-D structure of the region. In addition, the data can be compared to a computer database of, for example, 3-D structures stored in a data storage system.

Pathogenic Factors (PF) and Pathogenic Agents

The method of the invention involves, in part, the analysis of a pathogenesis factor region with low polymorphism.

As used herein, a "pathogenesis factor" ("PF") is a molecule or a molecular complex that is a component of a pathogenic agent, or an altered form of such a component. Thus, PF can be wild-type molecules or complexes containing wild-type molecules. They can also be molecules, or complexes of molecules, altered from the wild-type form by, for example, chemical or recombinant methodologies, but in a way that does not change the tertiary structure of the region referred to herein as the region with low polymorphism. Thus, in a PF that is such an altered molecule or is a complex containing such an altered molecule, the region with low polymorphism will have the same tertiary structure that it has in the native conformation of the wild-type molecule. PF can be physically associated with the pathogenic agent (e.g., as a cell membrane, cell wall, or viral coat component) or it can be released or secreted from the pathogenic agent.

As used herein, a "pathogenic agent" is a biological entity that causes pathological symptoms when present in a mammalian host. Thus a pathogenic agent can be, without limitation, an infectious agent (e.g., a virus, a prion, a bacterium, a yeast or other fungus, a mycoplasma, or a eukaryotic parasite such as a protozoan parasite, a nematode parasite, or a trematode parasite) or a tumor cell (e.g., a lung cancer or a breast cancer cell). Examples of relevant infectious agents include, without limitation, *Mycobacteria tuberculosis, Salmonella enteriditis, Listeria monocytogenes, M. leprae, Staphylococcus aureus, Escherichia coli, Streptococcus pneumoniae, Borrelia burgdorferi, Actillobacillls pleuropneumoniae, Helicobacter pylori, Neisseria meningitidis, Yersinia enterocolitica, Bordetella pertussis, Porphyromonas gingivalis,* mycoplasma, *Histoplasma capsulatum, Cryptococcus neoformans, Chlamydia trachomatis, Candida albicans, Plasmodium falciparum, Plasmodium vivax, Plasmodium malariae, Entamoeba histolytica, Toxoplasma brucei, Toxoplasma gondii, Leishmania major*, human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus.

Examples of tumor cells include cells from neural tissue cancer, melanoma, breast cancer, lung cancer, gastrointestinal cancer, ovarian cancer, testicular cancer, lung cancer, prostate cancer, cervical cancer, bladder cancer, vaginal cancer, liver cancer, renal cancer, bone cancer, a hematological cell cancer, and vascular tissue cancer.

PF can be composed of protein, nucleic acid (DNA or RNA), carbohydrate, lipid, or a combination of two or more of these. They will preferably have at least a component that is a polypeptide. Examples of relevant infectious agent proteins include, without limitation, the B subunit of heat labile enterotoxin of *E. coli* [Konieczny et al. (2000) FEMS Immunol. Med. Microbiol. 27(4):321-332]; heat-shock proteins, e.g., the *Y. enterocolitica* heat shock protein 60 [Konieczny et al. (2000) supra; Mertz et al. (2000) J. Immunol. 164(3): 1529-1537] and *M. tuberculosis* heat-shock proteins hsp60 and hsp70; the *Chlamydia trachomatis* outer membrane protein [Ortiz et al. (2000) Infect. Immun. 68(3): 1719-1723]; the *B. burgdorferi* outer surface protein [Chen et al. (1999) Arthritis Rheum. 42(9):1813-1823]; the *L. major* GP63 [White et al. (1999) Vaccine 17(17):2150-2161 (and published erratum in Vaccine 17(20-21):2755)]; the *N. meningitidis* meningococcal serotype 15 PorB protein [Delvig et al. (1997) Clin. Immunol. Immunopathol. 85(2); 134-142]; the *P. gingivalis* 381 fimbrial protein [Ogawa, (1994) J. Med. Microbiol. 41 (5):349-358]; the *E. coli* outer membrane protein F [Williams et al. (2000) Infect. Immun. 68(5):2535-2545]; influenza virus hemagglutinins and neuraminidases; retroviral (e.g., HIV) surface glycoproteins (e.g., I-V gp160/120), or retroviral tat or gag proteins. Examples of relevant molecules produced by tumor cells include: (a) tumor antigens such as prostate-specific membrane antigen (PSMA) [Israeli et al. (1993) Cancer Res. 53(2):227-230], a mucin such as MUC-1, or any other antigen expressed on the surface of tumor cells; and (b) tumor-produced angiogenic factors such as vascular endothelial growth factor (VEGF), VEGF-A, VEGF-B, VEGF-C, and VEGF-D [Detmar (2000) J. Investig. Dermatol. Symp. Proc. 5(1):20-23; Paweletz et al. (1989) Crit. Oncol. Hematol. 9(3):197-242].

In view of their role in binding of HIV or SIV to target cells, the CD4 binding site and the chemokine receptor binding site on gp120 would both, at first glance, seem to be good candidates regions for the development of vaccines to HIV and SIV However, there are two factors limiting the usefulness of these as candidates for vaccine development: (a) extensive inter- and intra-clade polymorphism of the residues surrounding these sites; and (b) a recessed plate-like structure of the region containing these sites which hinders access by antibodies. On the other hand, HIV gp41 and SIV gp41 have various regions that are of low polymorphism and are suitably positioned on an exposed surface of the polypeptide (see below). Moreover, gp41 is involved in the infection process in that, following binding of the appropriate sites to CD4 and the chemokine receptor on a target cell, the complex composed of three gp120/gp41 units undergoes a conformational change which results in the insertion of the fusion peptide of gp41 into the host cell membrane. It is this latter step that facilitates entry of the virus into the target cell. Finally, in support of gp41's being a good candidate for HIV and SIV vaccine development, there are number of existing monoclonal antibodies specific for the membrane proximal gp41 ectodomain that neutralize across HIV clades.

Both natural and vaccine-induced immunity to malaria (caused by the protozoan parasites of the genus *Plasmodium*) have been hampered by antigenic variability of key immune molecules. Nevertheless, the ability of radiation-attenuated sporozoites to induce sterile protective immunity in murine and primate models (including man) and the ability of antibodies from semi-immune individuals to partially protect against infection clearly indicate the possibility of developing malaria-specific vaccines. As the blood stage of malaria is most responsible for clinical pathology and red blood cells lack major histocompatibility complex (MHC) class I and class II molecules, induction of antibody (rather than cytotoxic T lymphocyte) responses to blood stage antigens is key to establishing immunity to the parasite. Appropriate blood stage antigens of *P. falciparum* include merozoite surface protein-1 (MSP-1), ring-infected erythrocyte surface antigen (RESA), Plasmodium falciparum erythrocyte membrane protein-1 (PfFMP-1), Plasmodium falciparum 332 antigen (Pf332), Rosettin, merozoite surface protein-2 (MSP-2), serine stretch protein (SERP), glutamate-rich protein (GLURP), apical membrane antigen-1 (AMA-1), and histidine-rich protein-2 (HRP-2). Importantly, the presence of antibodies against MSP-1 and RESA (Pf155) has been to shown to correlate with protection from clinical episodes of malaria.

In regard to prostate cancer, PSMA is a good candidate for vaccine development since, unlike prostate specific antigen (PSA), it is not secreted but is expressed on the cell surface only, and selectively on the surface of tumor cells.

As used herein, an "active conformation" of a region of a PF is the conformation of the region, in terms of the number of molecular subunits and the three-dimensional structure, in the PF (or in the wild-type version of the PF where the PF is an altered form of a wild-type molecule) as it occurs in a pathogenic agent. Where the region exists in more than one conformation in the pathogenic agent, the active conformation of the region is the conformation of the region as it exists in the pathogenic agent prior to a pathogenesis-promoting activity of the pathogenic agent. Such pathogenesis-promoting activities include, for example, the insertion of all or part of a component of an infectious agent into a host cell membrane preliminary to entry of the infectious agent into the host cell. Another example of a pathogenesis-promoting activity is the binding of a pathogenic agent to a surface molecule of a mammalian cell preliminary to entry of the infectious agent into the cell. An additional pathogenesis-promoting activity can be the binding of a pathogenic agent (e.g., an infectious agent or a tumor cell) to a host component (e.g., a cell surface receptor or an extracellular matrix component) so as to facilitate homing of the pathogenic agent to a tissue or organ of the host. A specific example of such a pathogenesis-promoting activity is the insertion of HIV envelope glycoprotein (gp120/gp41 complex) into a host cell membrane, a step that follows binding of the HIV virion to CD4 on the host cell surface and appears to induce entry of the virus into the host cell.

In a PF region with "low polymorphism" (as used herein), there is little to no variability in structure between individuals of a particular species or type expressing the PF. Where the PF is a protein, this limited variability is reflected in a highly conserved amino acid sequence.

For example, in contrast to CD4- and chemokine-binding sites in HIV-1 gp120, HIV-1 gp41 has low polymorphism in that little variability is seen between the amino acid sequences of the gp41 regions of different HIV-1 clades or between individual virions in a subject infected with HIV-1. Similarly, a region of low polymorphism region in a PF of a breast cancer cell (or a cell of a class of breast cancer characterized by expression of the PF of interest) from a particular subject has essentially the same structure in: (a) breast cancer cells of other subjects with the same class of breast cancer; and (b) other breast cancer cells from the same subject.

One means of representing the polymorphism in a polypeptide is to determine the Shannon entropy for each amino acid in the polypeptide [Shannon, The mathematical theory of communication. University of Illinois Press: Urbana, Ill. (1949); Litwin et al. In, Theoretical and Experimental Insights into Immunology. Eds. Perelson, A. S. and Weisbuch, G. Springer-Verlag (1992); Stewart et al. (1997) Mol. Immunol. 34(15):1067-1082]. Multiple alleles or variants of the polypeptide of interest are compared and the Shannon entropy (H) for each residue is determined according to the formula:

$$H = -\sum_{i=1}^{i=20} p_i \log_2 p_i$$

$p_i$ is the fraction of residues (among the all the variants/alleles compared) that are of amino acid type i.

Figure 1B:
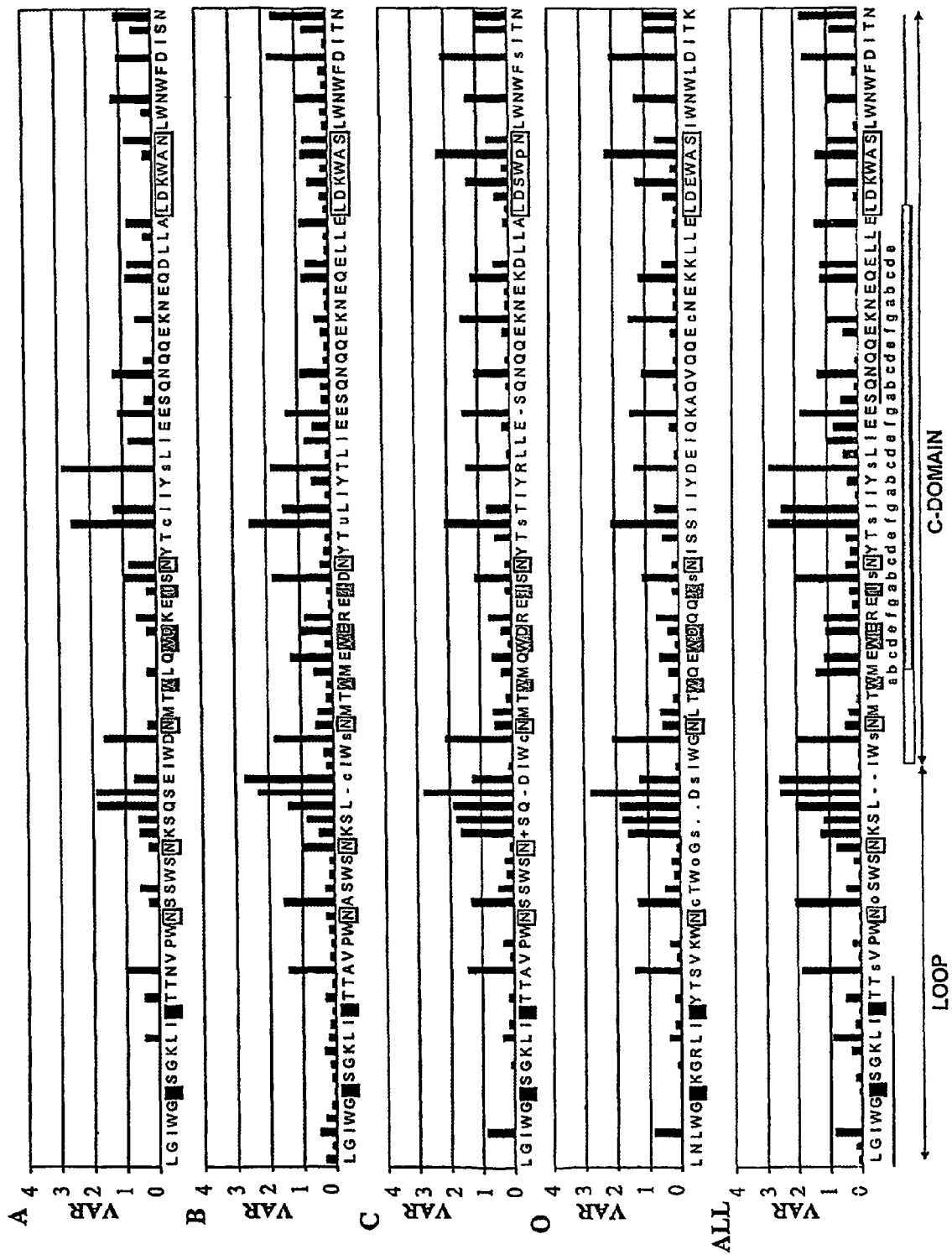
Figure 5:
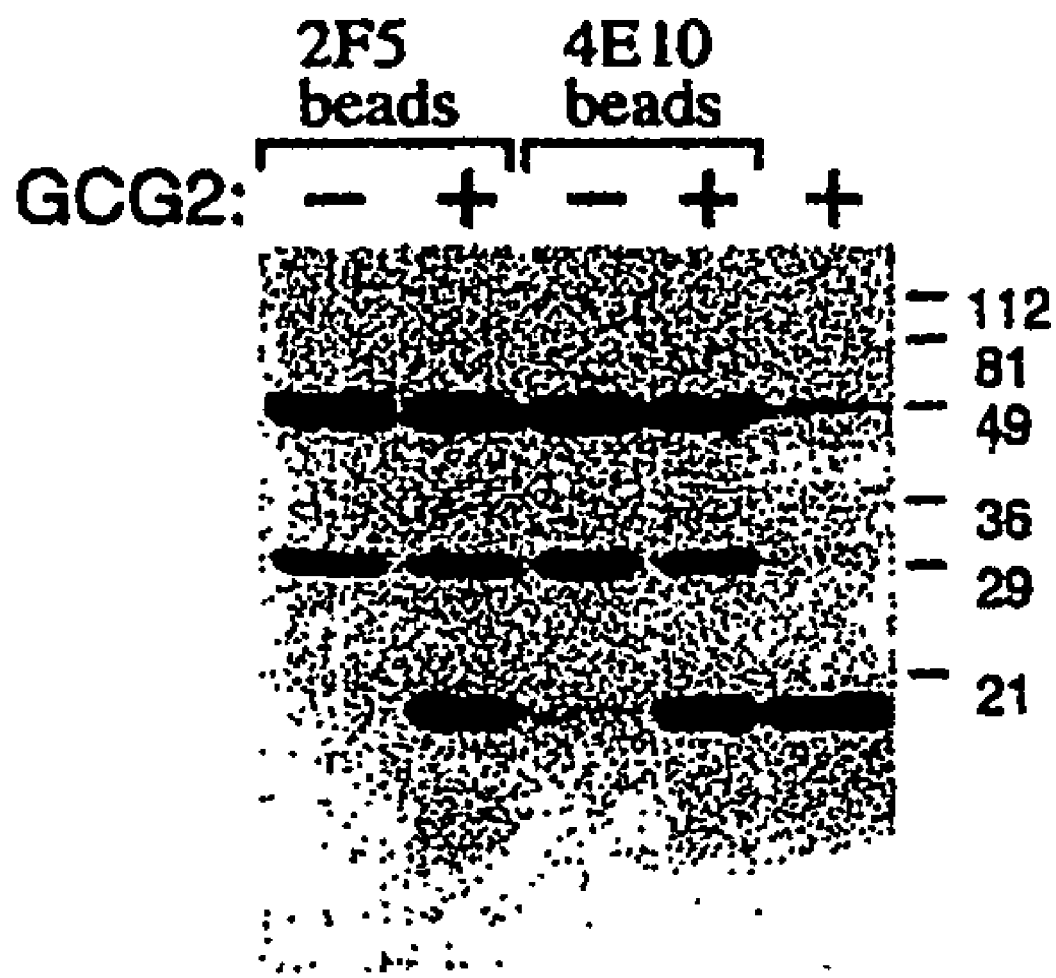
Figure 6:
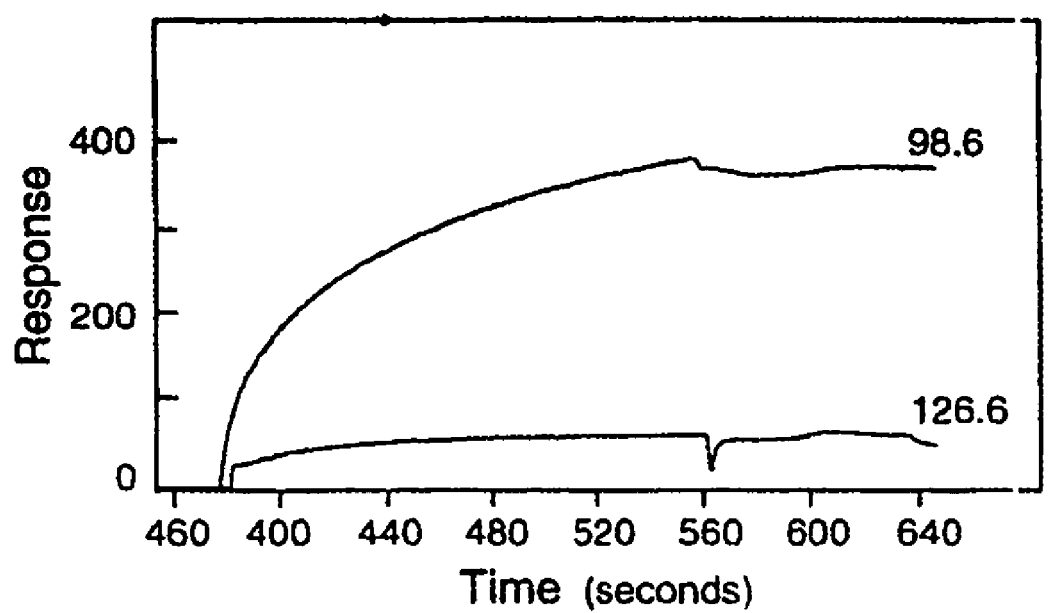
FIG. 6 is a line graph showing the Biosensor responses (over time) observed with a CM5 chip coated with either mAb 98.6 ("98.6") or mAb 126.6 ("126.6") and then exposed to a solution of GCG2 fusion protein.

For the 20 common amino acids, H can range from 0 (constant amino acid) to 4.32 (all amino acids represented equally). Sites at which H<2 are considered conserved and sites at which H>2 are considered not-conserved. By way of example, FIGS. 1A-B are bar charts showing (on the y-axis) the Shannon entropy for each amino acid residue as determined by comparing the amino acid sequences of HIV-1 gp41 ectodomains obtained from multiple mV-1 isolates from clades A (21 isolates; top chart), B (266 isolates; second chart), C (84 isolates; third chart) and O (10 isolates; fourth chart). The bottom chart ("ALL") shows the data obtained when all the isolates (454) from all clades were compared. For this analysis, a region with low polymorphism (an "LP region") is one containing nine or more consecutive residues, each having H≦1.3. The data shown for clades A and O should be treated with some caution since a rigorous Shannon entropy measure requires that a relatively high number of sequences (approximately 100) be compared. A consensus sequence for the relevant part of the polypeptide is shown below each row. As can be seen from FIG. 1; there are multiple regions of low variability.

However, low variability is not the only consideration in deciding upon a region of the molecule to focus on as a candidate for developing an immunogen of the invention. The region should be on an exposed surface of the protein and should preferably also neither contain nor be in close proximity to glycosylation sites on the polypeptide. LP regions may vary from one clade to another. In order to design a compound capable of eliciting a broad and general immune response, it is imperative to identify one or more LP regions that are common to all clades. Thus, for example, the epitope recognized by the 2F5 monoclonal antibody (the boxed sequence (LDKWAS) (SEQ ID NO:5) towards the C-terminus of the C-domain of the ALL bar chart in FIG. 1B) would appear to be a good target for a cross-clade immunogenic response. However, a more careful inspection indicates that the 2F5 monoclonal antibody epitope is within a LP region for clades A and B (i.e., a region of nine or more amino acid residues, each residue having H≦1.3), but not for clades C and O since in these clades the residue at the fifth position of the 2F5 monoclonal antibody epitope has H≧1.3.

For the purposes of the invention, a region of a protein with low polymorphism is a region containing at six or more (e.g., six, seven, eight, nine, ten, 11, 12, 13, 14, 15, 16, 18, 20, 24, 28, 35, 40, or more) consecutive amino acid residues, each amino acid residue having H≦2.0 (e.g., H≦1.8, ≦1.6, ≦1.4, ≦1.3, ≦1.2, ≦1.1, ≦1.0, ≦0.9, ≦0.8, ≦0.7, ≦0.6, ≦0.5, ≦0.4, ≦0.3, 0.2, or ≦0.1, or H=0). In view of the fact that they fulfill this criterion for low polymorphism and, in addition, are predicted to be on the surface of gp41 in its trimeric, prefusion state, a segment in the loop domain and a segment in the C-domain (or parts of the two segments or fragments containing either of the two segments) are promising candidates on which to perform the method of the invention. The amino acid sequences of these two segments in the consensus "ALL" chart (FIG. 1) are underlined and, in the "ALL" consensus sequence, the loop domain segment has the amino acid sequence LGIWGCSGKLICTT (SEQ ID NO:13) and the C-domain segment has the amino acid sequence SQN-QQEKNEQELL (SEQ ID NO:14).

The PF used for designing immunogens can be purified from natural sources (e.g., from any of the pathogenic agents listed herein). Smaller peptides (fewer than 100 amino acids long) and other non-protein PF or compounds of the invention can be conveniently synthesized by standard chemical means known to those in the art. In addition, both polypeptides and peptides, either as PF or compounds of the invention, can be manufactured by standard in vitro recombinant DNA techniques and in Vivo transgenesis using nucleotide sequences encoding the appropriate polypeptides or peptides (see Nucleic Acids section below). Methods well-known to those skilled in the art can be used to construct expression vectors containing relevant coding sequences and appropriate transcriptional/translational control signals. See for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

For the methods of the invention, it is generally required that the PF or PF fragments be highly purified. Methods for purifying biological macromolecules (e.g., proteins) are known in the art. The degree of purity of a PF or PF fragment can be measured by any appropriate method, e.g., column chromatography, polyacrylamide gel electrophoresis, or HPLC analysis.

Nucleic Acids

The invention also includes nucleic acids encoding compounds of the invention (see below). In addition, nucleic acid molecules encoding PF can be useful for the invention. For example, they can be used for producing the PF in order to carry out the structural analyses described herein. The nucleic acid molecules can be cDNA, genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules can contain naturally occurring sequences, or sequences that differ from those that occur naturally, but, due to the degeneracy of the genetic code, encode the same polypeptide. In addition, these nucleic acid molecules are not limited to coding sequences, e.g., they can include some or all of the non-coding sequences that lie upstream or downstream from a coding sequence.

The nucleic acid molecules can be synthesized (for example, by phosphoramidite-based synthesis) or obtained from a biological cell or infectious agent, such as a cell (e.g., a cancer cell) of a mammal or a virus.

In addition, the nucleic acid molecules of the invention, and those useful for the invention, include segments that are not found as such in the natural state. Thus, the invention encompasses recombinant nucleic acid molecules (for example, an isolated nucleic acid molecule encoding a compound of the invention) incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

The invention also encompasses: (a) vectors (see below) that contain any of the sequences encoding the compounds of the invention; (b) expression vectors that contain any of the foregoing coding sequences operably linked to any transcriptional/translational regulatory elements (examples of which are given below) necessary to direct expression of the coding sequences; and (c) genetically engineered host cells (see below) that contain any of the foregoing expression vectors and thereby express the nucleic acid molecules of the invention.

The transcriptional/translational regulatory elements referred to above and further described below include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the tr system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecule of the invention; insect cell systems infected with recombinant virus expression vectors (for example, baculovirus) containing the nucleic acid molecule of the invention; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a periostin nucleotide sequence; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors of the invention can then be used, for example, for large or small scale in vitro manufacture of a polypeptide PF or compound of the invention by methods known in the art. In essence, such methods involve culturing the cells under conditions that maximize production of the polypeptide and isolating the polypeptide from the cells or from the culture medium.

Data for Determining the 3-D Structure of a Molecule or Region of a Molecule

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography

X-ray crystallography is based on the diffraction of x-radiation of a characteristic wavelength by electron clouds surrounding the atomic nuclei in a crystal of the PF region of interest. The technique uses crystals of purified biological macromolecules (but these frequently include solvent components, co-factors, substrates, or other ligands) to determine near atomic resolution of the atoms making up the particular biological macromolecule. A prerequisite for solving the 3-D structure of the macromolecule by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the PF or PF fragments are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., Example 2 below and U.S. Pat. No. 5,790,421).

Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991]) Advances in Protein Chemistry, 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M Hepes, 2-4% butanol, 0.1M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306], an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see U.S. Pat. No. 5,597,457).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573, column 15.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from U.S. Pat. No. 6,093,573 and International Application Nos. PCT/US99/18441, PCT/US99/11913, and PCT/US00/03745.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenborn et al. (1990) Anal. Chem. 62(1):2-15; and Wider (2000), supra.

Any available method can be used to construct a 3-D model of a PF region of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

Designing Compounds of the Invention

Once the 3-D structure of a PF region of interest has been established using any of the above methods, a compound that has substantially the same 3-D structure (or contains a domain that has substantially the same structure) as the relevant PF region can be made. In this context, "has substantially the same 3-D structure" means that the compound includes one or more (e.g., one, two, three, four, five, six, seven, eight, nine, ten, 12, 15, 20, 30, 40, 50, 100, or more) epitopes with the ability to induce the production in a mammal (e.g., a human, non-human primate (e.g., a monkey or a chimpanzee), horse, cow, sheep, goat, pig, cat, dog, rabbit, guinea pig, rat, hamster, or mouse) of an antibody that binds to the region of the PF in its active conformation. One of skill in the art would know how to test a compound for such an ability.

With the above described 3-D structural data on hand and knowing the chemical structure (e.g., amino acid sequence in the case of a protein) of the PF region of interest, those of skill in the art would know how to make compounds with the above-described properties. Such methods include chemical synthetic methods and, in the case of proteins, recombinant methods (see above). For example, cysteine residues appropriately placed in a compound so as to form disulfide bonds can be used to constrain the compound or a domain of the compound in an appropriate 3-D structure. In addition, in a compound that is a polypeptide or includes a domain that is a polypeptide, one of skill in the art would know what amino acids to include and in what sequence to include them in order to generate, for example, α-helices, β structures, or sharp turns or bends in the polypeptide backbone.

While not essential, computer-based methods can be used to design the compounds of the invention. Appropriate computer programs include: LUDI (Biosym Technologies, Inc., San Diego, Calif.), Aladdin (Daylight Chemical Information Systems, Irvine, Calif.); and LEGEND [Nishibata et al. (1985) J. Med. Chem. 36(20):2921-2928].

The compounds of the invention can include, in addition, to the above described immunogenic domains, one or more domains that facilitate purification (e.g., poly-histidine sequences) or domains that serve to direct the compound to organs of the immune system, e.g., ligands or antibodies (including antibody fragments such Fab, F(ab')$_2$, or single chain Fv fragments) specific for cell surface components of cells of the immune system, e.g., the Flt3 ligand or antibodies specific for CD4, CD8, CD3, CD2, CD19, or CD20. Other useful domains include immune stimulatory cytokines (e.g., without limitation, interleukin (IL)-2, IL-4, IL-5, IL-6, IL-10, IL-13), adjuvant molecules (e.g., cholera toxin or E. coli heat labile toxin) or functional fragments of such molecules, i.e., those retaining at least some, e.g., 10%, 20%, 30%, 40%, 50%, 60%, 70%, 80%, 90%, or all, of the activity of the parent molecule, or at least the receptor-binding activity. All that is required in such multidomain compounds is that the immunogenic domain retains the 3-D structure it would have in the absence of the additional domains. Conjugation to make such multidomain compounds can be by chemical methods (e.g., Barrios et al. (1992) Eur. J. Immunol. 22:1365-1372]. Where the compound is a peptide, it can be produced as part of a recombinant protein, such as one that self-assembles into virus-sized particles (e.g., U.S. Pat. No. 4,918,166) that display the immunogenic peptide on the surface.

Compounds of the invention that are peptides also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of compounds of the invention that are peptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to elicit the production of antibodies cross-reactive with a selected peptide. Peptidomimetic compounds can have additional characteristics that enhance their ill vivo utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Determining the Immunogenicity of the Compounds of the Invention

A candidate compound can be tested for immunogenicity by any of a number of methods known in the art. For example, the test compound can administered to a test mammal (e.g., a human patient or volunteer, non-human primate (e.g., a monkey or a chimpanzee), horse, cow, sheep, goat, pig, cat, dog, rabbit, guinea pig, rat, hamster, or mouse). The test compound can be administered orally or transdermally, or injected (or infused) intravenously, subcutaneously, intramuscularly, intraperitoneally, intrarectally, intravaginally, intranasally, intragastrically, intratracheally, or intrapulmonarily. They can be delivered directly to an appropriate lymphoid tissue (e.g. spleen, lymph node, or mucosal-associated lymphoid tissue (MALT)). The test substance could be administered alone or with adjuvant, e.g., cholera toxin (CT), E. coli heat labile toxin (LT), mutant CT (MCT) [Yamamoto et al. (1997) J. Exp. Med. 185:1203-1210] and mutant *E. coli* heat labile toxin (MLT) (Di Tommaso et al. (1996) Infect. Immunity 64:974-979]. MCT and MLT contain point mutations that substantially diminish toxicity without substantially compromising adjuvant activity relative to that of the parent molecules. Other useful adjuvants include alum, Freund's complete and incomplete adjuvant, and RIBI. If desired, booster immunizations may be given once or several (two, three, four, eight or twelve, for example) times at various times (e.g., spaced one week apart). Antibody (e.g., IgG, IgM, or IgA) responses specific for the compound and/or for the PF from which the compound was derived can then be measured by testing for the presence of such antibodies systemically (e.g., in serum) or, for example, at various mucosal sites (e.g., in saliva or gastric and bronchioalveolar lavages) using in vitro assays familiar to those in the art, e.g., the enzyme-linked immunosorbent assay (ELISA). Alternatively, or in addition, since CD4+ T cell responses are generally required for antibody responses, in vitro CD4+ T cell responses to the test compound and/or the relevant PF can be measured using methods known in the art. Such methods include CD4+ T cell proliferation or lymphokine (e.g., interleukin-2, interleukin-4, or interferon-γ) production assays. In addition, in vivo skin tests can be performed on the test mammals. Such assays test for the both antibodies and pre-activated CD4+ T cells specific for the test antigen. A positive response within 12 hours is indicative of an antibody response while a response that is optimal between 48 and 96 hours indicates the presence of CD4+ T cells that have previously been exposed to the relevant antigen.

The same or identically treated mammals can also be tested for resistance to infection by a relevant infectious agent or for tumor development after injection or implantation of appropriate tumor cells. After immunization (as indicated above), the test mammals are injected or implanted with a single dose or various doses of the relevant infectious agent or tumor cells. The test mammals can be observed for pathologic symptoms familiar to those in the art, e.g., malaise, lack of appetite, morbidity and mortality. Alternatively, they may euthanized at various time points and their tissues (e.g., lung, liver, spleen, kidney or intestine) may be assayed for relative levels of the infectious agent or tumor cells by methods known to artisans of ordinary skill (e.g., viral plaque forming assays or immunocytochemical assays using antibodies specific for tumor cell markers). The data obtained with the test mammals can be compared to those obtained with a control group of mammals, e.g., mammals that were exposed to the diluent in which the test compound was dissolved or suspended (e.g. physiological saline) or adjuvant without the compound if adjuvant was used for immunization. Increased resistance of the test mammals to infection or tumor development, relative to the control mammals, would indicate that the test compound is an effective vaccine.

In vitro neutralization assays (e.g., see Example 4 below) familiar to those in the art can also be performed to test for the presence of infectious agent-specific neutralizing antibodies in samples (e.g., serum samples) obtained from the above described test and control mammals. In addition, sera from test and control subjects can be tested for the presence of antibodies that can kill tumor cells by, for example, complement-mediated lysis or antibody dependent cell-mediated cytotoxicity (ADCC) by methods known to those skilled in the art.

Methods of Activating an Immune Response

The invention features methods of activating mammalian immune responses in which cells of the immune system are exposed to one or more compounds of the invention.

The methods of the invention can be performed in vitro or in vivo. In vitro application of the compounds of the invention can be useful, for example, in basic scientific studies of immune mechanisms or for the production of antibodies, e.g., for use in studies on infection or cancer or for passive immunotherapy. In vitro activation with the compounds of the invention can also be used to obtain activated B lymphocytes useful for deriving monoclonal antibody-producing cell lines (e.g., human antibody-producing cell lines or hybridomas).

In the in vitro methods of the invention, lymphoid cells (including T and B lymphocytes) obtained from a mammalian subject are cultured with a compound of the invention. The lymphoid cells can be from a subject pre-exposed to the compound, to the PF from which the compound was derived, or to a pathogenic agent that produces the PF; alternatively, the donor of the lymphoid cells need not have been exposed to any of these entities. The cultures can be "restimulated" as often as necessary with either the compound or the PF. The cultures can also be monitored at various times to ascertain whether the desired level of immune reactivity (e.g., antibody production or CD4+ T cell activity) has been attained.

The compounds of the invention are generally useful for generating immune responses and as prophylactic vaccines or immune response-stimulating therapeutics. Thus, the responses elicited by the compounds need have neither prophylactic nor therapeutic efficacy. They can be used, for example, (a) to elicit large-quantities of antibodies in mammals (e.g., rabbits, goats, sheep, or horses) that are subsequently isolated from the animals and used for purposes such as antigen detection or purification, or (b) for immunization of animals (e.g., mice, rats, or hamsters) with a view to making monoclonal antibodies.

The compounds can also be used, for example, as vaccines or therapeutic agents against (a) infectious diseases due to any of the infectious agents listed herein; or (b) cancers such as any of those listed herein. The compounds can be useful in the prevention and/or therapy of diseases involving intracellular microorganisms (i.e., infectious agents that replicate inside a cell), e.g., viruses such as influenza virus or HIV, intracellular bacteria such *M. tuberculosis*, and intracellular protozoans such as *P. falciparum* or any of the other infectious agents listed herein. In addition, the compounds can be useful therapeutics for cancer (e.g., any of those recited above); in cases where a subject is at relatively high risk for a cancer (e.g., prostate cancer in men over 50 years of age, lung cancer in a tobacco smoker, or melanoma in a subject with multiple nevi), appropriate compounds can be used as prophylactic vaccines.

As used herein, "prophylaxis" can mean complete prevention of the symptoms of a disease, a delay in onset of the symptoms of a disease, or a lessening in the severity of subsequently developed disease symptoms. "Prevention" should mean that symptoms of the disease (e.g., an infection) are essentially absent. As used herein, "therapy" can mean a complete abolishment of the symptoms of a disease or a decrease in the severity of the symptoms of the disease. As used herein, a "protective" immune response is an immune response that is prophylactic and/or therapeutic.

The methods of the invention can be applied to a wide range of species, e.g., humans, non-human primates (e.g., monkeys), horses, cattle, pigs, sheep, goats, dogs, cats, rabbits, guinea pigs, hamsters, rats, and mice.

In one in vivo approach, the compound itself is administered to the subject. Generally, the compounds of the invention will be suspended in a pharmaceutically-acceptable carrier (e.g., physiological saline) and administered orally or transdermally or injected (or infused) intravenously, subcutaneously, intramuscularly, intraperitoneally, intrarectally, intravaginally, intranasally, intragastrically, intratracheally, or intrapulmonarily. They can be delivered directly to an appropriate lymphoid tissue (e.g. spleen, lymph node, or mucosal-associated lymphoid tissue (MALT)). A live cell vector containing a DNA encoding (a) the peptide compound or (b) a fusion protein containing the peptide compound, can be delivered orally or directly to the MALT. The dosage required depends on the route of administration, the nature of the formulation, the nature of the patient's illness, the subject's size, weight, surface area, age, and sex, other drugs being administered, and the judgment of the attending physician. Suitable dosages are in the range of 0.001-100.0 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery, particularly for oral delivery. The frequency of administration can be as indicated above in the section describing method for determining the immunogenicity of the compounds of the invention. In addition, the same adjuvants described in that section can be used.

Alternatively, a polynucleotide containing a nucleic acid sequence encoding a compound of interest can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), Mol. Cell. Biol. 12, 1043-1053; Todd et al. (1993), J. Exp. Med. 177, 1663-1674; Penix et al. (1993), J. Exp. Med. 178, 1483-1496]. Delivery of "naked DNA" (i.e., without a delivery vehicle) to an intramuscular, intradermal, or subcutaneous site is another means to achieve in vivo expression.

In the relevant polynucleotides (e.g., expression vectors) the nucleic acid sequence encoding the compound with an initiator methionine and optionally a targeting sequence is operatively linked to a promoter or enhancer-promoter combination. Promoters and enhancers are described above.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide that is capable of producing a medically desirable result (e.g., an antibody response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes and frequency of administration can be any of those listed above.

These methods of the invention can be applied to any of the diseases and species listed here. Methods to test whether a compound is therapeutic for or prophylactic against a particular disease are known in the art. Where a therapeutic effect is being tested, a test population displaying symptoms of the disease (e.g., cancer patients) is treated with a test compound of the invention, using any of the above described strategies. A control population, also displaying symptoms of the disease, is treated, using the same methodology, with a placebo. Disappearance or a decrease of the disease symptoms in the test subjects would indicate that the compound was an effective therapeutic agent.

By applying the same strategies to subjects prior to onset of disease symptoms (e.g., presymptomatic subjects considered to likely candidates for cancer development (see above) or experimental animals in which an appropriate disease spontaneously arises or can be deliberately induced, e.g., multiple murine cancers), the compounds can be tested for efficacy as prophylactic agents, i.e., vaccines. In this situation, prevention of onset of disease symptoms is tested. Analogous strategies can be used to test for the efficacy of the compounds in the prophylaxis of a wide variety of infectious diseases, e.g., those involving any of the microorganisms listed above.

The following examples are meant to illustrate, not limit, the invention.

EXAMPLES

The following examples describe experiments designed to generate an SIV-specific immunogen based on the 3-D structure of the ectodomains of SIV gp41 as they exist in the gp120/gp41 trimer prior to binding to CD4 and a chemokine receptor on appropriate target cells. An x-ray crystallographic analysis is performed on a trimer of SIV gp140 rather than a trimer of the g120/gp41 complex. SIV gp41 is a recombinant form of the ectodomains of SIV gp160 in which the primary and secondary cleavage sites between gp120 and gp41 are mutated to prevent cleavage into gp120 and the ectodomains of gp41. Recent results of chemical cross-linking, analytical ultracentrifugation, and mass spectrometry experiments indicate that secreted recombinant gp140 is, like wild-type gp120/gp41, a trimer [Chen et al. (2000) J. Biol. Chem. 45(10):34946-34953] The 3-D structure of gp41 in trimers of gp140 is likely to be substantially the same as in trimers of gp120/gp41 because gp41-specific antibodies that are conformationally specific (i.e., that do not bind to denatured gp41) bind to trimers of both gp140 and gp120/gp41.

Example 1

Production of Recombinant SIV gp140

Production of SIV gp140 in mammalian cells SIV gp140 from the SIV strain Mac23H pJ5 [Rud et al. In, Vaccines 92: Modern Approaches to New Vaccines Including Prevention of AIDS (Brown, F., Chanock, R. M., Ginsberg, H. S., and Lerner, R. A., eds) pp. 229-235, Cold Spring Harbor Laboratory, Cold Spring Harbor, N.Y., 1992] was expressed in CHO-Lec3.2.8.1 cells using an expression construct (pGP140) that was the same as pSIV-M [Rhodes et al. (1994) J. Gen. Virol. 75:207-213] but a shorter heterologous tissue plasminogen activator (tpA) leader sequence was used. The cDNA sequence (SEQ ID NO:1) encoding Mac23HpJ25 gp160 is shown in FIG. 2A and the amino acid sequence (SEQ ID NO:2) of Mac23HpJ25 gp160, including the leader peptide, is shown in FIG. 2B. The site at which the leader peptide is cleaved is indicated by a vertical line. In FIG. 3A is shown the cDNA sequence (SEQ ID NO:3) encoding gp140 in pGP140, including the heterologous tPA leader peptide. In FIG. 3B is shown the amino acid sequence (SEQ ID NO:4) of gp140, including the tPA leader peptide. The site at which the leader peptide is cleaved is indicated by a vertical line. Note that the two basic residues at the primary cleavage site (Lys-523) and a secondary cleavage site (Arg-512) between gp120 and gp41 of the Mac23HpJ5 gp160 have been replaced by glutamic acid residues to prevent cleavage of the gp140 molecule and to avoid shedding of gp120 that is observed with native constructs.

In brief, 20 μg of SalI-linearized pGP140 DNA was transfected into Lec3.2.8.1 cells by calcium phosphate precipitation. Transformants were selected in GMEM medium (Life Technologies. Inc., Carlsbad, Calif.) containing 25 μM methionine sulfoximine and assayed for secretion of soluble SIV gp140 by enzyme-linked immunosorbent assays (ELISA). Immulon™ plates (Dynatech Laboratories, Inc., Chantilly, Va.) were coated with anti-SIV ENV monoclonal antibody KK19 [Kent et al. (1991) Aids 5:829-836] by incubating the wells of the plates with a 4 μg/ml solution of the antibody overnight at 4° C.; non-specific protein binding sites in the wells were blocked with 1% solution of bovine serum albumin (BSA) in phosphate buffered saline (PBS) at room temperature for 2 hours. Cell culture supernatant (50 μl per well) from each transformant clone was added to the wells of the plates, which were incubated overnight at 4° C. The plates were washed with PBS containing 0.1% BSA and incubated with biotinylated anti-SIV ENV monoclonal antibody KK41 (0.2 μg/ml) [Kent et al. (1992) AIDS Res. Hum. Retroviruses 8:1147-1151] for 2 hours at room temperature. After washing again, the plates were developed with horseradish peroxidase-conjugated streptavidin (Sigma, St. Louis, Mo.). The highest expressing cells were chosen for rescreening with the same assay. The expression of gp140 was also confirmed by immunoprecipitation. Large scale production of SIV gp140 was carried out following a protocol previously described [Liu et al. (1996) J. Biol Chem. 271:33639-33646] in 175 $cm^2$ tissue culture flasks or 850 $cm^2$ roller bottles (Corning, Oneonta, N.Y.).

Production of SIV gp140 in Insect Cells

The pFBSIV-His1 expression vector was constructed to express SIV gp140 in insect cells using the Bac-to-Bac expression system (Life Technologies, Inc.). The polypeptide produced by pFBSIV-His1 includes gp140, the honey bee melittin secretion signal sequence at the N-terminus of gp140, and a hexahistidine sequence at the N-terminus of gp140 to facilitate purification by Nickel affinity chromatography. The coding sequence in pSIV-M was amplified by PCR using primers IG1 (5'-CGCGGATCCGACTCAATATGTCACAGTCTTTTAT-3') (SEQ ED NO:6) and IG2 (5'-GGCCGAATTCTATATCCAAGAAGCAAGG-3') (SEQ ID NO:7) to produce a DNA fragment encompassing the complete SIV gp140 coding sequence. The PCR product was digested with BamHI and EcoRI, gel-purified, and cloned into pMelBac (Invitrogen) to generate an intermediate construct pBacSIV-5, which was sequenced using primers to verify the entire sequence of SIV gp140 open reading frame. The coding sequence in pBacSIV-5 was then amplified using primers IG3 (5'-TTTATGGTCGTATACATTTCTTACATCTATGCGACTCAATATGTCACAGTC-3') (SEQ ID NO:8) and IG4 (5'-TAGTCTCATTGACCATGTCT-3') (SEQ ID NO:9). The resulting PCR product was reamplified using primers IG5 (5'-CGCGGATCCATGAAATTCTTAGTCAACGTTGCCCTTGTTTTTATGGTCGTATACATT-3') (SEQ ID NO:10) and IG4 to produce a 447-bp fragment, which was digested with BamHI and NsiI, gel-purified, and designated as fragment 1. This fragment allows fusion of the N terminus of SIV gp140 and the melittin secretion signal sequence. pBacSIV-5 was digested with NsiI and NcoI and a 1.5-kb fragment (designated fragment 2), which encompassed a major portion of SIV gp140 open reading frame, was gel-purified. To introduce a histidine tag at the C-terminus of SIV gp140, a 757-bp PCR product was amplified using pBacSIV-5 as template and IG6 (5'-GAGACCTCACGTGTAACT-3') (SEQ ID NO:11) and IG7 (5'-CCGGAATTCTCAATGATGATGATGATGATGAGTGCGACCTTCGATTTGTAT ATACTTATCCAAGA-3') (SEQ ID NO:12) as primers and digested with NcoI and EcoRI, gel-purified, and designated as fragment 3. Fragments 1, 2, and 3 were ligated together and cloned into pFastBac-1 (Life Technologies, Inc.), digested with BamHI and EcoRI, to give the expression construct pFBSIV-His1.

Recombinant baculovirus was generated according to the manufacturer's protocol and amplified in Sf9 insect cells in TNM-FH medium (Sigma). Expression of SIV gp140 was confirmed by a Western blot using sheep antisera against SIV envelope glycoprotein. The optimal amount of virus and postinfection harvest time was determined by small scale tests in 100-ml spinner flasks. Infected *Trichoplusia ni* (Hi-5) cells were found to secrete significantly more SIV gp140 than Sf9 cells as assessed by Western blotting. For large scale protein production, 10 liters of *T. ni* (Hi-5) cells ($2\times10^6$ cells/ml) in Ex-Cell 405 medium (JRH Biosciences) were infected at a multiplicity of infection of 2.5. Three days after infection, the supernatant was harvested by centrifugation and concentrated to 1 liter in a tangential flow filtration system, ProFlux M 12 (Millipore Corp.).

Purification of SIV gp140

The CHO Lec3.2.8.1 transfectant supernatants containing secreted SIV gp140 were harvested by centrifugation or by filtration through a Corning filter (0.22 mm). SIV gp140 was purified by an immunoaffinity chromatography using a mAb 17A11 affinity column (5-ml bed volume), where the monoclonal antibody 17A11 was cross-linked at 5 mg/ml to GammaBind™ Plus Sepharose (Amersham Pharmacia Biotech, Piscataway, N.J.) with dimethyl pimelimidate (Pierce Chemical Co., Rockford, Ill.). The supernatants were passed through the column with a flow rate of about 0.5 ml/min. After extensive washing with PBS the protein was eluted with 100 mM glycine (pH 3.0), followed by immediate neutralization with 2 M Tris-HCl (pH 8.0) and 150 mM NaCl.

SIV gp140 expressed from insect cells was purified by metal chelate affinity chromatography with ProBond™ resin (Invitrogen, Carlsbad, Calif.). Concentrated insect cell culture supernatants were immediately exchanged into 1× column buffer (25 mM sodium phosphate (pH 8.0), 250 mM NaCl) in a ProFlux M 12 flow filtration system to remove small molecules in the medium that interfere with the binding of His-tagged SIV gp140 to the nickel column. After centrifugation at 5000 rpm in a JA-14 rotor (Beckman, Fullerton, Calif.) for 15 minutes to remove insoluble materials, imidazole was added to a final concentration of 15 mM to reduce nonspecific binding to the resin. Batch binding was then performed at 4° C. for 3 hours. After packing the column (about 5-ml bed volume), the beads were washed by 100 ml of 1× column buffer containing 15 mM imidazole, followed by further washing with 50 ml of 40 mM imidazole in 1× column buffer. The protein was eluted with 300 mM imidazole in 1× column buffer. The fractions were analyzed by SDS-PAGE. The fractions containing SIV gp140 were pooled, concentrated, and further purified by gel filtration chromatography on Superdex 200™ or Superose 6™ (Amersham Pharmacia Biotech) with a buffer containing 25 mM Tris-HCl and 150 mM NaCl.

Production of SIV gp40 in Bacteria cDNA encoding SIV gp140 is cloned into a bacterial expression vector, e.g., pET11a. For bacterial expression, the resulting construct is transformed into *E. coli* strain BL21 (DE3) bacteria carrying a chromosomal copy of T7 RNA polymerase under control of the IPTG inducible lac promoter. An overnight preculture of a transformant colony in 10 ml of Luria both medium supplemented with ampicillin (0.1 mg/ml) is inoculated into 1 liter of Luria broth medium at 37° C. and the culture is grown to log phase. Overproduction of the protein is initiated by addition of IPTG (isopropyl-β-D-thiogalactopyranoside) to a final concentration of 1 mM. After a further 3 hour incubation, the cells are harvested by centrifugation and then lysed by sonication. The isolated inclusion bodies are solubilized with buffer A (0.2M Tris-HCl pH 9.5, 6M guanidinium-HCl, 0.1M DTT and 1 mM EDTA) overnight at 4° C. and the resulting solution is dialyzed with buffer A without DTT at 4° C. Refolding of gp140 is done by rapid dilution to a final protein concentration of approximately 20 µg/ml in a renaturation buffer (0.2M Tris-HCl, pH 9.5, 0.8M arginine, 0.2 mM reduced glutathione, 1 mM oxidized glutathione). After incubation at 4° C. with stirring for 24 hours, the refolding solution is concentrated and dialyzed against PBS buffer. The refolded protein is further purified by immunoaffinity chromatography using a conformation dependent mAb (e.g., the 2F5 mAb) coupled to GammaBind Plus Sepharose. Aggregates and monomers are removed by Superdex 200 gel filtration column. Similarly, variants starting at different positions after the V3 loop and prior to the start of gp41 can be genetically engineered as well, expressed and refolded as potential protein vaccine immunogens.

Example 2

Crystallization and X-ray Crystallographic Analysis of SIV gp140 Trimers

X-ray crystallographic analyses are performed on SIV gp140 produced by recombinant mammalian, bacterial, and insect cells (see above). A critical factor for the production of useful crystals is both the chemical and size homogeneity of the macromolecule sample. A major factor contributing to size heterogeneity of glycoproteins is heterogeneous glycosylation. Proteins that are monodisperse under aqueous conditions have a probability of 75% of yielding crystals suitable for x-ray crystallography while polydisperse disperse samples have only a 10% probability of doing so [Sali (1998) Nature Struc. Biol. 5, 1029-1032]. Prior to crystallization, the SIV gp140 sample is analyzed with an instrument (Dyna Pro-ms/x; Protein Solutions, Lakewood, N.J.) designed to obtain a measurement of the degree of size homogeneity of the sample.

The Hampton sparse matrix crystallization screening protocol [Jancarik et al. (1991). J. Appl. Cryst. 24: 409-411) is used to ascertain optimal crystallization conditions. The effectiveness of this technique is based on known crystallization conditions for a variety of protein molecules. This sampling technique allows a quick test of wide ranges of pH, buffer type, precipitants, and some commonly used additives for the initial trial. Three categories of precipitants (salts (e.g. ammonium sulfate), PEG (e.g., PEG 4000), and organic solvents are tested. The hanging-droplet vapor diffusion method of crystallization is used such that, for each condition, as little as 1 µl of protein solution (at about 15-20 mg/ml) is used. One-2 mg protein is sufficient for testing 100 different conditions.

The additives used for crystallization can be very important. For example, the detergent β-octyl-glucopyranoside has in some cases been found to be invaluable [e.g., Casanovas et al. (1997) Nature 387: 312-315]. This detergent shields the hydrophobic surface of the protein. Glycerol is also known to be useful in crystallizing flexible proteins [Sousa et al. (1990) Methods: A Companion to Methods in Enzymology 1, 50-56]. Glycerol was also useful in converting twinning crystals into single crystals [Tan (1997) Proc. Natl. Acad. Sci. USA 94:12303-12308]. In addition, $Na_2SO_4$ dramatically improves the diffraction quality of crystals [Tong (1996) Nature 383: 272-275].

One x-ray crystallographic method of obtaining a novel 3-D structure is the multiple-isomorphous replacement (NMR) method. By examining the amino acid sequence of the protein, a favorable heavy atom-containing compound in which to soak the protein crystals is selected. A number of x-ray crystallographic data sets are collected using soaked and unsoaked crystals. Data sets obtained with an unsoaked crystal are compared to those obtained with soaked crystals to see whether there is any heavy atom binding. This is done by calculating a difference Patterson map. Sometimes a single heavy atom derivative will provide adequate initial phasing as a starting point. If not, other heavy atom-containing compounds are tested. It has been found that xenon is a good anomalous scattering center [Schiltz et al. (1995) Structure 3: 309-316]. The Molecular Structure Corporation (MSC) (Woodlands, Tex.) manufactures a device called Cryo-Xe-Siter™, which allows the introduction of xenon into protein crystals. According to a survey by MSC, the success rate is as high as 50%.

Another technique that has been extremely successful in the protein crystallography field is the MAD (multi-wavelength anomalous dispersion) method [Hendrickson (1991) Science 254, 51-58). About 2-4 data sets are collected from one single frozen crystal on the synchrotron, each using a slightly different wavelength near the absorption edge of the anomalous scattering centers. These data sets are in principle sufficient to obtain phases and solve the structure. To use the MAD method, one can make a seleno-methionine mutant protein and use the selenium as the anomalous scattering center for MAD data collection [Lustbader et al. (1995) Endocrinology 136: 640-650]. The mutant crystal is in general highly isomorphous to the wild type crystal because it avoids non-isomorphism introduced by heavy atom binding. Although the difference in the number of electrons between sulfur and selenium is only 18, the difference in scattering factor is sufficient to produce prominent peaks in the conventional isomorphous difference Patterson even using the data collected with an in-house x-ray source at the Dana Farber Cancer Institute [Wang (1995) Proc Natl Acad Sci USA 92, 5714-5718]. The selenium-based MAD phasing has become popular for another two reasons. First, the MAD data collection technique using the synchrotron has become routine. Second, there are programs that make it easier to locate the Se sites in crystals. These include SOLVE (Terwilliger et al. (1999) Acta Crystallogr. D Biol. Crystallogr. 55:849-61) and SnB, which is an implementation of the direct method [Hauptman (1999). Acta Crystallogr. A 55:891-900; Weeks (1999) Acta Crystallogr. D Biol. Crystallogr. 55:492-500].

Yet another x-ray crystallographic method is the molecular replacement method. In this method, diffraction data obtained on a new molecule of interest are phased using the 3-D coordinates of another molecule whose 3-D structure is known and can thus be employed as a search model for phasing. A powerful computer program AMoRe [Navaza (1994). Acta Cryst. A50: 157-163] is used to implement the method. A good search model is crucial to yield a correct result with molecular replacement. A problem with the method is that one does not know beforehand exactly how homologous the chosen search model is to the molecule of interest. One way to get around the burden is to take a so-called composite model, i.e., to superimpose several homologous molecules together as a search model. The composite model is then the average structure of several known molecules. Thus, for example, the several known structures of the gp41 ectodomain, or segments thereof, [Weissenhorn et al. (1997) Nature 387:426-430; Chan et al. (1997) Cell 89:263-273; Tan et al. (1998) Proc. Natl. Acad. Sci. USA. 94:12303-12308] could be superimposed to create a search model for the gp41 ectodomain in the gp140 trimer.

Example 3

Designing an Immunogenic Compound Based on the 3-D Structure of the Ectodomain of gp41 in the SIV gp140 Trimer Once the 3-D structure of SIV gp41 in its trimeric, prefusion state is obtained, the information is used to design a candidate immunogen. Given that the 3-D structure of the gp41 region in the gp140 (gp120/gp41) trimer is presently unknown, it is not possible to describe all potential avenues of design. A few examples are presented. One anticipated scenario is that the gp41 fusion peptide and the N-terminal trimeric peptide are buried in the axial groove between the gp120 protomers within the native trimer, leaving only the C-terminal peptide accessible to antibody attack: If this is the case, the C-terminal segment can be produced in E. coli or by peptide synthesis, adopting trimeric or non-trimeric conformation as the case may be. NMR or x-ray crystallography can then be used to show parity of the relevant segment in the mini-protein and the x-ray crystallographically-defined gp140 trimer structures. Alternatively, if this region is exposed but extensively constrained by structural interactions with gp120 or other gp41 components in achieving the native structure, additional domains must be appended. In the latter case, a non-native interaction domain from protein G, immunoglobulin, CD2 or other domains that can be used to facilitate the native fold of the gp41 graft can be generated. Eukaryotic and prokaryotic production is tested in parallel and structural authenticity documented by NMR and/or crystallography. Key parameters for the choice of additional domains to be incorporated into the mini-protein construct are ease of production and the potential to target dendritic cells (i.e., interdigitating dendritic cells) for optimization of immunogenicity. For example, Flt3 ligand, which stimulates growth of dendritic cells and could serve as a targeting vector to bring the mini-protein antigen to dendritic cells, could be co-incorporated with the immunogenic domain.

Example 4

Testing a Candidate Immunogenic Compound for Immunogenicity

Compounds designed and produced as described in Example 3 are tested in test animals. Animals of choice are rabbits, guinea pigs, or rhesus monkeys. The test animals are injected with and without an adjuvant (see above), by various routes, e.g., parenteral (e.g., intravenous, subcutaneous, or intramuscular), mucosal (e.g., intranasal, intrarectal, or intragastric), and with various frequencies. At various time points, the animals are bled and sera are extracted from the blood. The sera are tested for the presence of antibodies that bind to the test compound, to SIV gp41, to SIV gp140, to SIV gp160, and to intact SIV virions by any of a number of methods known to those in the art. In addition, the sera are tested for the presence of antibodies that neutralize SIV using assays familiar to investigators in the art [see, for example, Cho et al. (2001) J. Virol. 75(5):2224-2234]. Multiple strains of SIV are tested. Cells used for testing are whole peripheral blood mononuclear cells (PBMC), T cell lines (e.g., the CEMx174 cell line), or macrophage cell lines. PBMC can be activated (e.g., by a lectin such concanavalin A or phytohemagglutin) or resting.

Thus, for example, neutralization assays are performed on the molecularly cloned SIV stocks SIVmac239 and SIVsmH-4, and on the uncloned stocks SIV/DeltaB670 and SIVmac251 (mac32H (pJ5) equivalent). Virus stocks are prepared in H9 cells except for SIVmac239, which was produced in human PBMC. The SIVmac251 stock is extensively passaged in T cell lines. Cell free virus (50 µl containing 0.5 to 1 ng of SIV p27) is added to multiple dilutions of the test sera in 100 µl of growth medium in triplicate wells of 96-well tissue culture plates, which are incubated at 37° C. for 30 minutes before addition of CEMx174 cells ($10^5$ cells in 100 µl per well). Cell densities are reduced several-fold and medium is replaced after 3 days of incubation. The incubation is continued until virus-induced syncytium formation and cell killing are observed microscopically in wells incubated in the absence of test sera. Neutralization is determined by staining viable cells with Finters's neutral red in poly-L-lysine coated plates and measuring the $A_{540}$ of each well. Neutral red uptake by CEMx174 cells is linear from $3.1 \times 10^4$ to $5 \times 10^5$ viable cells/well, corresponding to $A_{540}$ values of 0.25 to 1.6. Percent protection is calculated by the difference in $A_{540}$ between test wells (wells containing cells plus virus plus test sera) and virus control wells (wells containing cells plus virus), divided by the difference in $A_{540}$ between cell control wells (wells containing cells only) and virus control wells.

Data are expressed as $ID_{50}$, which is the dilution of serum necessary to protect cells from virus-induced death to a level of 50%.

In addition to in vitro neutralization assays, in vivo protection assays such as those described generally above can be performed.

A compound demonstrating immunogenicity by any of the above assays can be manufactured by any of the methods described herein.

While the above examples describe experiments dealing with an SIV analysis, those of skill in the art will appreciate that the analysis can be readily adapted to the production of an HIV- (e.g., HIV-1- or HIV-2-) specific immunogenic compound.

Example 5

Generation of an HIV-1 Immunogen

A genetic construct encoding a fusion protein including an HIV-1 gp41 ectodomain was generated by PCR and cloned into the T7 promoter-containing expression vector pET11a. The genetic construct contained cDNA encoding, 5' to 3', domains consisting of: (a) 58 amino acids of the B1 IgG binding domain of streptococcal protein G ("GB 1"); (b) 57 amino acids of the C terminal ectodomain (cte) of HIV-1 strain HIV-lada (clade B) gp41; and (c) a 31 amino acid, mutated segment of the *Saccharomyces cerevisiae* leucine zipper protein GCN4. The amino acid sequence (SEQ ID NO:15) of the fusion protein, designated GCG2, is shown in FIG. 4A; the first amino acid in each domain is indicated in italics.

The 57 amino acid HIV-1 cte domain (SEQ ID NO:16) (FIG. 4B) included an amino acid sequence (SEQ ID NO:17) (FIG. 4C) corresponding to the C-domain sequence (having the amino acid sequence SEQ ID NO:14 shown in the "ALL" chart in FIG. 1) that, on account its low polymorphism and its predicted location on the surface of gp41 in its trimeric, prefIusion state (see above), is considered a promising candidate for immunogen development. The GB1 domain was included in GCG2 to facilitate purification and to enhance the immunogenicity and solubility of the protein. The GCN4 domain was included in GCG2 to enhance trimerization of the protein so as to mimic the conformation of the cte fragment as it would occur in a native. gp120/gp41 complex.

GCG2 was produced in BL21 (DE3) *E. coli* bacteria essentially as described above for SIV gp140 and was purified by IgG affinity, ion exchange, and gel filtration chromatography. One hundred mg of soluble GCG2 was produced from 1 liter of bacteria.

As shown by immunoprecipitation, the broadly neutralizing anti-mAbs 2F5 and 4E10 both bound GCG2 (FIG. 5). In addition, the ability of two mAbs (98.6 and 126.6) that recognize immunodominant cluster II of gp41 to bind to GCG2 were tested by Biosensor analysis. mAb 98.6 (or mAb 126.6) was bound to a CM5 chip which was then exposed to purified GB1 domain to prevent non-specific binding of GCG2 to the Fc domain of the chip-bound mAb. GCG2 was incubated with purified Fc fragments (also to prevent non-specific binding of GCG2 to the Fc domain of the mAb on the chip) and then passed over the chip in the Biosensor to measure binding to the chip-bound mAb. A control Biosensor response obtained when GCG2 was analyzed in the same way but with a control mAb of irrelevant specificity bound to the chip was subtracted from the responses observed with the 98.6 and 126.6 mAbs. While GCG2 bound to mAb 98.6, no significant binding was detected with mAb 126.6 (FIG. 6). Since mAb 98.6 recognizes immunodominant cluster II in both pre-hairpin and hairpin conformations of gp41 and mAb recognizes immunodominant cluster II in only the hairpin conformation of gp41, the above data indicate that, in GCG2, the HIV cte domain is in the pre-hairpin conformation. gp41 in an HIV-1 virion assumes the pre-hairpin conformation subsequent to binding of a relevant gp120/gp41 complex to CD4 and a coreceptor on a potential host cell (e.g., a T cell or a macrophage). By assuming this pre-hairpin conformation, gp41 becomes capable of inserting its amino-terminal fusion-peptide domain into the cell membrane of the potential host cell. Insertion of gp41 into the cell membrane facilitates fusion with the cell membrane and hence infection of the host cell by the virion. It seems likely thus that GCG2 would be an immunogen capable of eliciting the production (in appropriate mammalian subjects) of antibodies that bind to gp41 in its pre-hairpin conformation. By binding in such a highly selective manner to gp41 as it exists in virions at the stage immediately prior to fusion of HIV-1 with a host cell membrane, these antibodies would likely be potent inhibitors of infection of cells by mV-1.

A number of embodiments of the invention have been described. Nevertheless, it will be understood that various modifications may be made without departing from the spirit and scope of the invention. Accordingly, the invention is limited only by the following claims.

What is claimed is:

1. A computer-assisted method of determining whether a compound is immunogenic, the method requiring use of a programmed computer comprising a processor and an input device, the method comprising:
   (a) providing a pathogenesis factor (PF), or a fragment of a PF, comprising a region with low polymorphism, wherein the region is in an active conformation;
   (b) obtaining data on the region in the active conformation, wherein the data can be used to determine the three-dimensional structure of the region in the active conformation;
   (c) inputting to the input device the data;
   (d) determining, using the processor, the three-dimensional structure of the region in the active conformation;
   (e) designing a compound comprising a domain that includes at least one epitope that is likely to induce the production in a mammal of an antibody that binds to the region in the active conformation;
   (f) producing the compound; and
   (g) determining whether the compound elicits an antibody response in a mammalian host, wherein an antibody of the response binds to the region in the active conformation.

2. A process of manufacturing a compound, the process comprising: carrying out the method of claim 1; and, after determining that the compound elicits an antibody response, manufacturing the compound.

3. The method of claim 1, wherein the PF is a component, or an altered form of a component, of an infectious microorganism.

4. The method of claim 3, wherein the infectious microorganism is a microorganism that replicates inside a cell.

5. The method of claim 4, wherein the microorganism is a virus.

6. The method of claim 5, wherein the virus is a retrovirus.

7. The method of claim 6, wherein the retrovirus is simian immunodeficiency virus (SIV) or human immunodeficiency virus (HIV).

8. The method of claim 4, wherein the microorganism is a protozoan parasite.

9. The method of claim 8, wherein the protozoan parasite is a malarial protozoan parasite.

10. The method of claim 9, wherein the PF is merozoite surface protein-1 (MSP-1) or ring-infected erythrocyte surface antigen (RESA).

11. The method of claim 9, wherein the PF is selected from the group consisting of Plasmodium falciparum erythrocyte membrane protein-1 (PfEMP-1), Plasmodium falciparum 332 antigen (Pf332), Rosettin, merozoite surface protein-2 (MSP-2), serine stretch protein (SERP), glutamate-rich protein (GLURP), apical membrane antigen-1 (AMA-1), and histidine-rich protein-2 (HRP-2).

12. The method of claim 1, wherein the PF is: (a) a naturally occurring polypeptide; (b) an altered form of a naturally occurring polypeptide; or (c) a molecular complex comprising two or more subunits, each subunit being either of (a) or (b).

13. The method of claim 12, wherein the PF comprises a complex of retroviral envelope glycoproteins.

14. The method of claim 13, wherein the PF comprises three recombinant SIV gp140 polypeptides.

15. The method of claim 1, wherein the PF is a component, or an altered form of a component, of a cancer cell.

16. The method of claim 15, wherein the PF is prostate-specific membrane antigen (PSMA).

17. The method of claim 3, wherein the microorganism is a bacterium.

18. The method of claim 5, wherein the PF, or a wild-type form of the PF, mediates entry of the microorganism into a cell.

19. The method of claim 18, wherein the cell is a CD4+ cell.

20. The method of claim 19, wherein the CD4+ cell is a T cell.

21. The method of claim 19, wherein the CD4+ cell is a monocyte or a macrophage.

22. The method of claim 18, wherein the cell is an erythrocyte.

23. The method of claim 1, wherein the PF is provided in a crystalline form and the data are a criteria data set comprising three-dimensional atomic coordinates.

24. A method of determining whether a compound is immunogenic, the method comprising:

designing a compound comprising a domain that includes at least one epitope that is likely to elicit an antibody response in a mammal, wherein an antibody of the response binds to a region in an active conformation, and wherein the designing uses a three-dimensional structure of a pathogenesis factor (PF), or fragment of the pathogenesis factor, comprising the region with low polymorphism and being in an active conformation;

producing the compound; and determining whether the compound elicits an antibody response in a mammalian host, wherein an antibody of the response binds to the region in the active conformation.

25. The method of claim 24, further comprising determining the three-dimensional structure of the PF.

26. The method of claim 24, wherein the PF is provided in a crystalline form and the data are a criteria data set comprising three-dimensional atomic coordinates.

27. The method of claim 24, wherein the PF is a component, or an altered form of a component, of an infectious microorganism.

28. The method of claim 27, wherein the infectious microorganism is a microorganism that replicates inside a cell.

29. An isolated compound compnsing SEQ ID NO: 15, wherein said compound composes a domain that includes at least one epitope that induces the production in a mammal of an antibody that binds to a region of a pathogenesis factor (PF), or a fragment of a PF, with low polymorphism, the region being in an active conformation.

* * * * *

UNITED STATES PATENT AND TRADEMARK OFFICE
CERTIFICATE OF CORRECTION

PATENT NO. : 8,275,595 B2
APPLICATION NO. : 10/486278
DATED : September 25, 2012
INVENTOR(S) : Ellis L. Reinherz et al.

It is certified that error appears in the above-identified patent and that said Letters Patent is hereby corrected as shown below:

On the Title Page of the Patent, after "PCT Pub. Date: Feb. 27, 2003", and before "Prior Publication Data", please add new section:
-- Related U.S. Application Data
(60)    Provisional application No. 60/312,276, filed on August 14, 2001. --

Title Page, Column 2, Line 2, delete "ACids REsearch" and insert -- Acids Research --, therefor.

In Column 54, Line 14, in Claim 18, delete "claim 5," and insert -- claim 4, --, therefor.

In Column 54, Line 51, in Claim 29, delete "compnsing SEQ ID NO: 15," and insert -- comprising SEQ ID NO: 15, --, therefor.

In Column 54, Line 52, in Claim 29, delete "composes" and insert -- comprises --, therefor.

Signed and Sealed this
Fourth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,275,595 B2
APPLICATION NO. : 10/486278
DATED : September 25, 2012
INVENTOR(S) : Reinherz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
Tenth Day of June, 2014

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 2634
<212> TYPE: DNA
<213> ORGANISM: Simian immunodeficiency virus

<400> SEQUENCE: 1
atgggatgtc ttgggaatca gctgcttatc gccatcttgc ttttaagtgt ctacgggatc      60
tattgtactc aatatgtcac agtcttttat ggtgtaccag cttggaggaa tgcgacaatt     120
cccctcttct gtgcaaccga gaatagggat acttggggaa caactcagtg cctaccagat     180
```

```
aatggtgatt attcagaatt ggcccttaac gttacagaaa gctttgatgc ctgggagaat    240
acagtcacag aacaggcaat agaggatgta tggcaactct ttgagacctc aataaagcct    300
tgtgtaaaat tatccccatt atgcattact atgagatgca ataaaagtga dacagataaa    360
tggggattga caaaatcatt aacaacaaca gcaccaacag caccaacggc agcatcaaaa    420
atagacatgg tcaatgagac tagttcttgt ataactcatg ataattgcac aggcttggaa    480
caagagcaaa tgataggctg taaattcaac atgacagggt taaaagaga caagacaaag    540 gagtacaatg aaacttggta ctctacagat ttggtttgtg aacaagggaa tagcactgat    600
aatgaaagta gatgctacat gaatcactgt aacacttcta ttatccaaga gtcttgtgac    660
aagcattatt gggatactat tagatttagg tattgtgcac ctccaggtta tgctttgctt    720
agatgtaatg acacaaatta ttcaggcttt atgcctaaat gttctaaggt ggtggtctct    780
tcatgcacaa ggatgatgga cacagact tctacttggt ttggctttaa tggaactaga    840
gcagaaaata gaacttatat ttactggcat ggtagggata ataggactat aattagttta    900
aataagtatt ataatctaac aatgaaatgt agaagaccag gaaataagac agttttacca    960
gtcaccatta tgtctggatt ggttttccac tcacaaccaa tcaatgatag gccaaagcag   1020
gcatggtgtt ggtttggagg aaattggaag gatgcaataa aagagatgaa gcagaccatt   1080
gtcaaacatc ccaggtatac tggaactaac aatactgata aaatcaattt gacggctcct   1140
agaggaggag atccggaagt taccttcatg tggacaaatt gcagaggaga gttcctctac   1200
tgtaaaatga attggtttct aaattgggta gaagataggg atgtaactaa ccagaggcca   1260
aaggaacggc atagaaggaa ttacgtgcca tgtcatatta gacaaataat caacacttgg   1320
cataaagtag gcaaaatgt ttatttgcct ccaagagagg gagacctcac gtgtaactcc   1380
acagtgacca gtctcatagc aaacatagat tggactgatg gaaaccaaac taatatcacc   1440
atgagtgcag aggtggcaga actgtatcga ttggaattgg gagattataa attagtagag   1500
atcactccaa ttggcttggc ccccacagat gtgaagaggt acactactgg tggcacctca   1560
agaaataaaa gagggtcttt gtgctagggt tccttgggtt ttctcgcaac ggcaggttct   1620
gcaatgggcg cggcgtcgtt gacgctgacc gctcaatccc ggactttatt ggctgggata   1680
gtgcagcaac agcaacagct gttggacgtg tcaagagac aacaagaatt gttgcgactg   1740
accgtctggg gaacaaagaa cctccagact agggtcactg ccatcgagaa gtacttaaag   1800
gaccaggcgc agctgaatgc ttggggatgt gcgtttagac aagtctgcca cactactgta   1860
ccatggccaa atgcaagtct aacaccagac tggaacaatg atacttggca agagtgggag   1920
cgaaaggttg acttcttgga ggaaaatata acagccctcc tagaagaggc acaaattcaa   1980
caagagaaga acatgtatga attacaaaag ttgaatagct gggatgtgtt tggcaattgg   2040
tttgaccttg cttcttggat aaagtatata caatatggag tttatatagt tgtaggagta   2100
atactgttaa gaatagtgat ctatatagta caaatgctag ctaagttaag acaggggtat   2160
aggccagtgt tctcttcccc accctcttat ttccagcaga cccatatcca acaggacccg   2220
gcactgccaa ccagagaagg caaagaagga gacggtggag aaggcggtgg caacagctcc   2280
tggccttggc agatagaata tattcatttc ctgatccgcc aactgatacg cctcttgact   2340
tggctattca gcaactgcag aaccttgcta tcgagcatca accagatcct ccaaccaata   2400
ctccagaggc tctctgcggc cctacagaga attcgagaag tcctcaggac tgaactgacc   2460
tacctacaat atgggtggag ctatttccag gaggcggtcc aagtcggctg gagatctgcg   2520
acagagactc ttgcgggcgc gtggggagac ttatgggaga ctccttaggag aggtggaaga   2580
```
tggatactcg caatccctag gaggattaga caagggcttg agctcactct cttg        2634

<210> SEQ ID NO 2
<211> LENGTH: 878
<212> TYPE: PRT
<213> ORGANISM: Simian immunodeficiency virus

<400> SEQUENCE: 2

```
Met Gly Cys Leu Gly Asn Gln Leu Leu Ile Ala Ile Leu Leu Leu Ser
 1               5                  10                  15

Val Tyr Gly Ile Tyr Cys Thr Gln Tyr Val Thr Val Phe Tyr Gly Val
            20                  25                  30

Pro Ala Trp Arg Asn Ala Thr Ile Pro Leu Phe Cys Ala Thr Glu Asn
        35                  40                  45

Arg Asp Thr Trp Gly Thr Thr Gln Cys Leu Pro Asp Asn Gly Asp Tyr
    50                  55                  60

Ser Glu Leu Ala Leu Asn Val Thr Glu Ser Phe Asp Ala Trp Glu Asn
65                  70                  75                  80

Thr Val Thr Glu Gln Ala Ile Glu Asp Val Trp Gln Leu Phe Glu Thr
                85                  90                  95

Ser Ile Lys Pro Cys Val Lys Leu Ser Pro Leu Cys Ile Thr Met Arg
            100                 105                 110

Cys Asn Lys Ser Glu Thr Asp Lys Trp Gly Leu Thr Lys Ser Leu Thr
        115                 120                 125

Thr Thr Ala Pro Thr Ala Pro Thr Ala Ala Ser Lys Ile Asp Met Val
    130                 135                 140

Asn Glu Thr Ser Ser Cys Ile Thr His Asp Asn Cys Thr Gly Leu Glu
145                 150                 155                 160

Gln Glu Gln Met Ile Gly Cys Lys Phe Asn Met Thr Gly Leu Lys Arg
                165                 170                 175

Asp Lys Thr Lys Glu Tyr Asn Glu Thr Trp Tyr Ser Thr Asp Leu Val
            180                 185                 190

Cys Glu Gln Gly Asn Ser Thr Asp Asn Glu Ser Arg Cys Tyr Met Asn
        195                 200                 205

His Cys Asn Thr Ser Ile Ile Gln Glu Ser Cys Asp Lys His Tyr Trp
    210                 215                 220

Asp Thr Ile Arg Phe Arg Tyr Cys Ala Pro Pro Gly Tyr Ala Leu Leu
225                 230                 235                 240

Arg Cys Asn Asp Thr Asn Tyr Ser Gly Phe Met Pro Lys Cys Ser Lys
                245                 250                 255

Val Val Val Ser Ser Cys Thr Arg Met Met Glu Thr Gln Thr Ser Thr
            260                 265                 270

Trp Phe Gly Phe Asn Gly Thr Arg Ala Glu Asn Arg Thr Tyr Ile Tyr
        275                 280                 285

Trp His Gly Arg Asp Asn Arg Thr Ile Ile Ser Leu Asn Lys Tyr Tyr
    290                 295                 300

Asn Leu Thr Met Lys Cys Arg Arg Pro Gly Asn Lys Thr Val Leu Pro
305                 310                 315                 320

Val Thr Ile Met Ser Gly Leu Val Phe His Ser Gln Pro Ile Asn Asp
                325                 330                 335

Arg Pro Lys Gln Ala Trp Cys Trp Phe Gly Gly Asn Trp Lys Asp Ala
            340                 345                 350

Ile Lys Glu Met Lys Gln Thr Ile Val Lys His Pro Arg Tyr Thr Gly
        355                 360                 365
```

-continued

```
Thr Asn Asn Thr Asp Lys Ile Asn Leu Thr Ala Pro Arg Gly Gly Asp
            370                 375                 380

Pro Glu Val Thr Phe Met Trp Thr Asn Cys Arg Gly Glu Phe Leu Tyr
385                 390                 395                 400

Cys Lys Met Asn Trp Phe Leu Asn Trp Val Glu Asp Arg Asp Val Thr
                405                 410                 415

Asn Gln Arg Pro Lys Glu Arg His Arg Arg Asn Tyr Val Pro Cys His
            420                 425                 430

Ile Arg Gln Ile Ile Asn Thr Trp His Lys Val Gly Lys Asn Val Tyr
            435                 440                 445

Leu Pro Pro Arg Glu Gly Asp Leu Thr Cys Asn Ser Thr Val Thr Ser
450                 455                 460

Leu Ile Ala Asn Ile Asp Trp Thr Asp Gly Asn Gln Thr Asn Ile Thr
465                 470                 475                 480

Met Ser Ala Glu Val Ala Glu Leu Tyr Arg Leu Glu Leu Gly Asp Tyr
                485                 490                 495

Lys Leu Val Glu Ile Thr Pro Ile Gly Leu Ala Pro Thr Asp Val Lys
                500                 505                 510

Arg Tyr Thr Thr Gly Gly Thr Ser Arg Asn Lys Arg Gly Val Phe Val
            515                 520                 525

Leu Gly Phe Leu Gly Phe Leu Ala Thr Ala Gly Ser Ala Met Gly Ala
530                 535                 540

Ala Ser Leu Thr Leu Thr Ala Gln Ser Arg Thr Leu Leu Ala Gly Ile
545                 550                 555                 560

Val Gln Gln Gln Gln Leu Leu Asp Val Val Lys Arg Gln Gln Glu
                565                 570                 575

Leu Leu Arg Leu Thr Val Trp Gly Thr Lys Asn Leu Gln Thr Arg Val
            580                 585                 590

Thr Ala Ile Glu Lys Tyr Leu Lys Asp Gln Ala Gln Leu Asn Ala Trp
            595                 600                 605

Gly Cys Ala Phe Arg Gln Val Cys His Thr Thr Val Pro Trp Pro Asn
610                 615                 620

Ala Ser Leu Thr Pro Asp Trp Asn Asn Asp Thr Trp Gln Glu Trp Glu
625                 630                 635                 640

Arg Lys Val Asp Phe Leu Glu Glu Asn Ile Thr Ala Leu Leu Glu Glu
                645                 650                 655

Ala Gln Ile Gln Gln Glu Lys Asn Met Tyr Glu Leu Gln Lys Leu Asn
            660                 665                 670

Ser Trp Asp Val Phe Gly Asn Trp Phe Asp Leu Ala Ser Trp Ile Lys
            675                 680                 685

Tyr Ile Gln Tyr Gly Val Tyr Ile Val Val Gly Val Ile Leu Leu Arg
            690                 695                 700

Ile Val Ile Tyr Ile Val Gln Met Leu Ala Lys Leu Arg Gln Gly Tyr
705                 710                 715                 720

Arg Pro Val Phe Ser Ser Pro Ser Tyr Phe Gln Gln Thr His Ile
                725                 730                 735

Gln Gln Asp Pro Ala Leu Pro Thr Arg Glu Gly Lys Glu Gly Asp Gly
            740                 745                 750

Gly Glu Gly Gly Gly Asn Ser Ser Trp Pro Trp Gln Ile Glu Tyr Ile
                755                 760                 765

His Phe Leu Ile Arg Gln Leu Ile Arg Leu Leu Thr Trp Leu Phe Ser
            770                 775                 780

Asn Cys Arg Thr Leu Leu Ser Arg Ala Tyr Gln Ile Leu Gln Pro Ile
785                 790                 795                 800
```

Leu Gln Arg Leu Ser Ala Ala Leu Gln Arg Ile Arg Glu Val Leu Arg
                805                 810                 815

Thr Glu Leu Thr Tyr Leu Gln Tyr Gly Trp Ser Tyr Phe Gln Glu Ala
        820                 825                 830

Val Gln Val Gly Trp Arg Ser Ala Thr Glu Thr Leu Ala Gly Ala Trp
            835                 840                 845

Gly Asp Leu Trp Glu Thr Leu Arg Arg Gly Gly Arg Trp Ile Leu Ala
    850                 855                 860

Ile Pro Arg Arg Ile Arg Gln Gly Leu Glu Leu Thr Leu Leu
865                 870                 875

<210> SEQ ID NO 3
<211> LENGTH: 2069
<212> TYPE: DNA
<213> ORGANISM: Simian immunodeficiency virus

<400> SEQUENCE: 3
aggatgcaat gaagagaggg ctctgctgtg tgctgctgct gtgtggagca gtcttcgttt      60
cgcccagcgc tagcactcaa tatgtcacag tctttttatgg tgtaccagct tggaggaatg    120
cgacaattcc cctcttctgt gcaaccgaga atagggatac ttggggaaca actcagtgcc    180
taccagataa tggtgattat tcagaattgg cccttaacgt tacagaaagc tttgatgcct    240
gggagaatac agtcacagaa caggcaatag aggatgtatg gcaactcttt gagacctcaa    300
taaagccttg tgtaaaatta tccccattat gcattactat gagatgcaat aaaagtgaga    360
cagataaatg gggattgaca aaatcattaa caacaacagc accaacagca ccaacggcag    420
catcaaaaat agacatggtc aatgagacta gttcttgtat aactcatgat aattgcacag    480
gcttggaaca gagcaaatg ataggctgta aattcaacat gacagggtta aaaagagaca    540
agacaaagga gtacaatgaa acttggtact ctacagattt ggtttgtgaa cagggaata    600 gcactgataa tgaaagtaga tgctacatga atcactgtaa cacttctatt atccaagagt    660
cttgtgacaa gcattattgg gatactatta gatttaggta ttgtgcacct ccaggttatg    720
ctttgcttag atgtaatgac acaaattatt caggctttat gcctaaatgt tctaaggtgg    780
tggtctcttc atgcacaagg atgatggaga cacagacttc tacttggttt ggctttaatg    840
gaactagagc agaaaataga acttatattt actggcatgg tagggataat aggactataa    900 ttagttaa taagtattat aatctaacaa tgaaatgtag aagaccagga ataagacag    960 ttttaccagt caccattatg tctggattgg ttttccactc acaaccaatc aatgataggc   1020
caaagcaggc atggtgttgg tttggaggaa attggaagga tgcaataaaa gagatgaagc   1080
agaccattgt caacatccc aggtatactg aactaacaa tactgataaa atcaatttga   1140
cggctcctag aggaggagat ccggaagtta ccttcatgtg acaaattgc agaggagagt   1200 tcctctactg taaatgaat tggtttctaa attgggtaga agatagggat gtaactaacc   1260
agaggccaaa ggaacggcat agaaggaatt acgtgccatg tcatattaga caaataatca   1320
acacttggca taagtaggc aaaaatgttt atttgcctcc aagagaggga gacctcacgt   1380
gtaactccac agtgaccagt ctcatagcaa acatagattg gactgatgga accaaaacta   1440
atatcaccat gagtgcagag gtggcagaac tgtatcgatt ggaattggga gattataaat   1500
tagtagagat cactccaatt ggcttggccc ccacagatgt gaaggagtac actactggtg   1560
gcacctcaag aaatgaaaga gggtctttt gctagggtt cttgggtttt ctcgcaacgg   1620
caggttctgc aatgggcgcg gcgtcgttga cgctgaccgc tcaatcccgg actttattgg   1680

-continued

```
ctgggatagt gcagcaacag caacagctgt tggacgtggt caagagacaa caagaattgt   1740
tgcgactgac cgtctgggga acaaagaacc tccagactag ggtcactgcc atcgagaagt   1800
acttaaagga ccaggcgcag ctgaatgctt ggggatgtgc gtttagacaa gtctgccaca   1860
ctactgtacc atggccaaat gcaagtctaa caccagactg gaacaatgat acttggcaag   1920
agtgggagcg aaaggttgac ttcttggagg aaaatataac agccctccta gaagaggcac   1980
aaattcaaca agagaagaac atgtatgaat tacaaaagtt gaatagctgg gatgtgtttg   2040
gcaattggtt tgaccttgct tcttggata                                     2069

<210> SEQ ID NO 4
<211> LENGTH: 686
<212> TYPE: PRT
<213> ORGANISM: Simian immunodeficiency virus
<400> SEQUENCE: 4

Met Asp Ala Met Lys Arg Gly Leu Cys Cys Val Leu Leu Leu Cys Gly
 1               5                  10                  15

Ala Val Phe Val Ser Pro Ser Ala Ser Thr Val Phe Tyr Gly Val Pro
            20                  25                  30

Ala Trp Arg Asn Ala Thr Ile Pro Leu Phe Cys Ala Thr Glu Asn Arg
        35                  40                  45

Asp Thr Trp Gly Thr Thr Gln Cys Leu Pro Asp Asn Gly Asp Tyr Ser
    50                  55                  60

Glu Leu Ala Leu Asn Val Thr Glu Ser Phe Asp Ala Trp Glu Asn Thr
65                  70                  75                  80

Val Thr Glu Gln Ala Ile Glu Asp Val Trp Gln Leu Phe Glu Thr Ser
                85                  90                  95

Ile Lys Pro Cys Val Lys Leu Ser Pro Leu Cys Ile Thr Met Arg Cys
            100                 105                 110

Asn Lys Ser Glu Thr Asp Lys Trp Gly Leu Thr Lys Ser Leu Thr Thr
        115                 120                 125

Thr Ala Pro Thr Ala Pro Thr Ala Ala Ser Lys Ile Asp Met Val Asn
    130                 135                 140

Glu Thr Ser Ser Cys Ile Thr His Asp Asn Cys Thr Gly Leu Glu Gln
145                 150                 155                 160

Glu Gln Met Ile Gly Cys Lys Phe Asn Met Thr Gly Leu Lys Arg Asp
                165                 170                 175

Lys Thr Lys Glu Tyr Asn Glu Thr Trp Tyr Ser Thr Asp Leu Val Cys
            180                 185                 190

Glu Gln Gly Asn Ser Thr Asp Asn Glu Ser Arg Cys Tyr Met Asn His
        195                 200                 205

Cys Asn Thr Ser Ile Ile Gln Glu Ser Cys Asp Lys His Tyr Trp Asp
    210                 215                 220

Thr Ile Arg Phe Arg Tyr Cys Ala Pro Pro Gly Tyr Ala Leu Leu Arg
225                 230                 235                 240

Cys Asn Asp Thr Asn Tyr Ser Gly Phe Met Pro Lys Cys Ser Lys Val
                245                 250                 255

Val Val Ser Ser Cys Thr Arg Met Met Glu Thr Gln Thr Ser Thr Trp
            260                 265                 270

Phe Gly Phe Asn Gly Thr Arg Ala Glu Asn Arg Thr Tyr Ile Tyr Trp
        275                 280                 285

His Gly Arg Asp Asn Arg Thr Ile Ile Ser Leu Asn Lys Tyr Tyr Asn
    290                 295                 300

Leu Thr Met Lys Cys Arg Arg Pro Gly Asn Lys Thr Val Leu Pro Val
```

```
                305                 310                 315                 320
Thr Ile Met Ser Gly Leu Val Phe His Ser Gln Pro Ile Asn Asp Arg
            325                 330                 335
Pro Lys Gln Ala Trp Cys Trp Phe Gly Gly Asn Trp Lys Asp Ala Ile
            340                 345                 350
Lys Glu Met Lys Gln Thr Ile Val Lys His Pro Arg Tyr Thr Gly Thr
            355                 360                 365
Asn Asn Thr Asp Lys Ile Asn Leu Thr Ala Pro Arg Gly Gly Asp Pro
            370                 375                 380
Glu Val Thr Phe Met Trp Thr Asn Cys Arg Gly Glu Phe Leu Tyr Cys
385                 390                 395                 400
Lys Met Asn Trp Phe Leu Asn Trp Val Glu Asp Arg Asp Val Thr Asn
            405                 410                 415
Gln Arg Pro Lys Glu Arg His Arg Arg Asn Tyr Val Pro Cys His Ile
            420                 425                 430
Arg Gln Ile Ile Asn Thr Trp His Lys Val Gly Lys Asn Val Tyr Leu
            435                 440                 445
Pro Pro Arg Glu Gly Asp Leu Thr Cys Asn Ser Thr Val Thr Ser Leu
450                 455                 460
Ile Ala Asn Ile Asp Trp Thr Asp Gly Asn Gln Thr Asn Ile Thr Met
465                 470                 475                 480
Ser Ala Glu Val Ala Glu Leu Tyr Arg Leu Glu Leu Gly Asp Tyr Lys
            485                 490                 495
Leu Val Glu Ile Thr Pro Ile Gly Leu Ala Pro Thr Asp Val Lys Glu
            500                 505                 510
Tyr Thr Thr Gly Gly Thr Ser Arg Asn Glu Arg Gly Val Phe Val Leu
            515                 520                 525
Gly Phe Leu Gly Phe Leu Ala Thr Ala Gly Ser Ala Met Gly Ala Ala
            530                 535                 540
Ser Leu Thr Leu Thr Ala Gln Ser Arg Thr Leu Leu Ala Gly Ile Val
545                 550                 555                 560
Gln Gln Gln Gln Gln Leu Leu Asp Val Val Lys Arg Gln Gln Glu Leu
                565                 570                 575
Leu Arg Leu Thr Val Trp Gly Thr Lys Asn Leu Gln Thr Arg Val Thr
            580                 585                 590
Ala Ile Glu Lys Tyr Leu Lys Asp Gln Ala Gln Leu Asn Ala Trp Gly
            595                 600                 605
Cys Ala Phe Arg Gln Val Cys His Thr Thr Val Pro Trp Pro Asn Ala
            610                 615                 620
Ser Leu Thr Pro Asp Trp Asn Asn Asp Thr Trp Gln Glu Trp Glu Arg
625                 630                 635                 640
Lys Val Asp Phe Leu Glu Glu Asn Ile Thr Ala Leu Leu Glu Glu Ala
            645                 650                 655
Gln Ile Gln Gln Glu Lys Asn Met Tyr Glu Leu Gln Lys Leu Asn Ser
            660                 665                 670
Trp Asp Val Phe Gly Asn Trp Phe Asp Leu Ala Ser Trp Ile
            675                 680                 685

<210> SEQ ID NO 5
<211> LENGTH: 6
<212> TYPE: PRT
<213> ORGANISM: Artificial Sequence
<220> FEATURE:
<223> OTHER INFORMATION: epitope

<400> SEQUENCE: 5
```

Leu Asp Lys Trp Ala Ser
 1               5

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
cgcggatccg actcaatatg tcacagtctt ttat                                34

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
ggccgaattc tatatccaag aagcaagg                                       28

<210> SEQ ID NO 8
<211> LENGTH: 51
<212> TYPE: DNA
<213> ORGANISM: Artificial Sequence
<220> FEATURE:
<223> OTHER INFORMATION: primer

<400> SEQUENCE: 8
tttatggtcg tatacatttc ttacatctat gcgactcaat atgtcacagt c             51

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tagtctcatt gaccatgtct                                                20

<210> SEQ ID NO 10
<211> LENGTH: 55
<212> TYPE: DNA
<213> ORGANISM: Artificial Sequence
<220> FEATURE:
<223> OTHER INFORMATION: primer

<400> SEQUENCE: 10
cgcggatcca tgaaattctt agtcaacgtt gcccttgttt ttatggtcgt ataca          55

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
gagacctcac gtgtaact                                                  18

<210> SEQ ID NO 12
<211> LENGTH: 63
<212> TYPE: DNA

-continued

```
<213> ORGANISM: Artificial Sequence
<220> FEATURE:
<223> OTHER INFORMATION: primer

<400> SEQUENCE: 12
ccggaattct caatgatgat gatgatgatg agtgcgacct tcgatttgta tatacttatc    60
caa                                                                  63

<210> SEQ ID NO 13
<211> LENGTH: 14
<212> TYPE: PRT
<213> ORGANISM: Artificial Sequence
<220> FEATURE:
<223> OTHER INFORMATION: consensus sequence

<400> SEQUENCE: 13

Leu Gly Ile Trp Gly Cys Ser Gly Lys Leu Ile Cys Thr Thr
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: consensus sequence

<400> SEQUENCE: 14

Ser Gln Asn Gln Gln Glu Lys Asn Glu Gln Glu Leu Leu
 1               5                  10

<210> SEQ ID NO 15
<211> LENGTH: 146
<212> TYPE: PRT
<213> ORGANISM: HIV-1

<400> SEQUENCE: 15

Met Gln Tyr Lys Leu Ile Leu Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Ala Asn Asp Asn Gly Val Asp Gly Glu Trp Thr Tyr Asp Asp Ala
         35                  40                  45

Thr Lys Thr Phe Thr Val Thr Glu Gly Ser Thr Trp Met Glu Trp Glu
     50                  55                  60

Arg Glu Ile Glu Asn Tyr Thr Gly Leu Ile Tyr Thr Leu Ile Glu Glu
 65                  70                  75                  80

Ser Gln Asn Gln Gln Glu Lys Asn Glu Gln Asp Leu Leu Ala Leu Asp
                 85                  90                  95

Lys Trp Ala Ser Leu Trp Asn Trp Phe Asp Ile Ser Asn Trp Leu Trp
            100                 105                 110

Tyr Ile Lys Met Lys Gln Ile Glu Asp Lys Ile Glu Glu Ile Leu Ser
        115                 120                 125

Lys Ile Tyr His Ile Glu Asn Glu Ile Ala Arg Ile Lys Lys Leu Ile
    130                 135                 140

Gly Glu
145

<210> SEQ ID NO 16
<211> LENGTH: 57
<212> TYPE: PRT
<213> ORGANISM: HIV-1
```

```
<400> SEQUENCE: 16

Thr Trp Met Glu Trp Glu Arg Glu Ile Glu Asn Tyr Thr Gly Leu Ile
 1               5                  10                  15

Tyr Thr Leu Ile Glu Glu Ser Gln Asn Gln Gln Glu Lys Asn Glu Gln
            20                  25                  30

Asp Leu Leu Ala Leu Asp Lys Trp Ala Ser Leu Trp Asn Trp Phe Asp
        35                  40                  45

Ile Ser Asn Trp Leu Trp Tyr Ile Lys
    50                  55

<210> SEQ ID NO 17
<211> LENGTH: 13
<212> TYPE: PRT
<213> ORGANISM: HIV-1

<400> SEQUENCE: 17

Ser Gln Asn Gln Gln Glu Lys Asn Glu Gln Asp Leu Leu
 1               5                  10

<210> SEQ ID NO 18
<211> LENGTH: 166
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 129
<223> OTHER INFORMATION: Xaa = Asp, Glu, His, Lys, or Arg
<220> FEATURE:
<221> NAME/KEY: VARIANT
<222> LOCATION: 133
<223> OTHER INFORMATION: Xaa = Ala, Cys, Asp, Gly, Asn, Pro, Ser, Thr,
      or Val

<400> SEQUENCE: 18

Ala Val Gly Ile Gly Ala Val Phe Ile Gly Phe Leu Gly Ala Ala Gly
 1               5                  10                  15

Ser Thr Met Gly Ala Ala Ser Ile Thr Leu Thr Val Gln Ala Arg Gln
            20                  25                  30

Leu Leu Ser Gly Ile Val Gln Gln Gln Ser Asn Leu Leu Arg Ala Ile
        35                  40                  45

Glu Ala Gln Gln His Leu Leu Lys Leu Thr Val Trp Gly Ile Lys Gln
    50                  55                  60

Leu Gln Ala Arg Val Leu Ala Val Glu Arg Tyr Leu Arg Asp Gln Gln
65                  70                  75                  80

Leu Leu Gly Ile Trp Gly Cys Ser Gly Lys Leu Ile Cys Thr Thr Asn
                85                  90                  95

Val Pro Trp Asn Ser Ser Trp Ser Asn Lys Ser Gln Ser Glu Ile Trp
            100                 105                 110

Asp Asn Met Thr Trp Leu Gln Trp Asp Lys Glu Ile Ser Asn Tyr Thr
        115                 120                 125

Xaa Ile Ile Tyr Xaa Leu Ile Glu Glu Ser Gln Asn Gln Gln Glu Lys
    130                 135                 140

Asn Glu Gln Asp Leu Leu Ala Leu Asp Lys Trp Ala Asn Leu Trp Asn
145                 150                 155                 160

Trp Phe Asp Ile Ser Asn
                165

<210> SEQ ID NO 19
<211> LENGTH: 166
```

```
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 109
<223> OTHER INFORMATION: Xaa = Asp or Glu
<220> FEATURE:
<221> NAME/KEY: VARIANT
<222> LOCATION: 110
<223> OTHER INFORMATION: Xaa = Asp, Glu, His, Lys, or Arg
<220> FEATURE:
<221> NAME/KEY: VARIANT
<222> LOCATION: 113
<223> OTHER INFORMATION: Xaa = Ala, Cys, Asp, Gly, Asn, Pro, Ser, Thr,
      or Val
<220> FEATURE:
<221> NAME/KEY: VARIANT
<222> LOCATION: 129
<223> OTHER INFORMATION: Xaa = Ala, Gly, or Ser

<400> SEQUENCE: 19

Ala Val Gly Ile Gly Ala Ile Phe Leu Gly Phe Leu Gly Ala Ala Gly
 1               5                  10                  15

Ser Thr Met Gly Ala Ala Ser Ile Thr Leu Thr Val Gln Ala Arg Gln
             20                  25                  30

Leu Leu Ser Gly Ile Val Gln Gln Gln Asn Asn Leu Leu Arg Ala Ile
         35                  40                  45

Glu Ala Gln Gln His Leu Leu Gln Leu Thr Val Trp Gly Ile Lys Gln
 50                  55                  60

Leu Gln Ala Arg Val Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Xaa Xaa Ile Trp
            100                 105                 110

Xaa Asn Met Thr Trp Met Glu Trp Glu Arg Glu Ile Asp Asn Tyr Thr
        115                 120                 125

Xaa Leu Ile Tyr Thr Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asp Ile Thr Asn
                165

<210> SEQ ID NO 20
<211> LENGTH: 166
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 106
<223> OTHER INFORMATION: Xaa = His, Lys, or Arg
<220> FEATURE:
<221> NAME/KEY: VARIANT
<222> LOCATION: 109, 137
<223> OTHER INFORMATION: Xaa = Asp or Glu
<220> FEATURE:
<221> NAME/KEY: VARIANT
<222> LOCATION: 113
<223> OTHER INFORMATION: Xaa = Asp, Glu, His, Lys, or Arg
<220> FEATURE:
<221> NAME/KEY: VARIANT
<222> LOCATION: 129, 163
<223> OTHER INFORMATION: Xaa = Ala, Cys, Asp, Gly, Asn, Pro, Ser, Thr,
```

```
              or Val
<220> FEATURE:
<221> NAME/KEY: VARIANT
<222> LOCATION: 156
<223> OTHER INFORMATION: Xaa = Cys, Asp, Glu, His, Lys, Asn, Gln, Arg,
      Ser, or Thr

<400> SEQUENCE: 20

Ala Val Gly Ile Gly Ala Val Phe Leu Gly Phe Leu Gly Ala Ala Gly
 1               5                  10                  15

Ser Thr Met Gly Ala Ala Ser Ile Thr Leu Thr Val Gln Ala Arg Gln
             20                  25                  30

Leu Leu Ser Gly Ile Val Gln Gln Gln Ser Asn Leu Leu Arg Ala Ile
         35                  40                  45

Glu Ala Gln Gln His Met Leu Gln Leu Thr Val Trp Gly Ile Lys Gln
 50                  55                  60

Leu Gln Thr Arg Val Leu Ala Ile Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ser Ser Trp Ser Asn Xaa Ser Gln Xaa Asp Ile Trp
            100                 105                 110

Xaa Asn Met Thr Trp Met Gln Trp Asp Arg Glu Ile Ser Asn Tyr Thr
        115                 120                 125

Xaa Thr Ile Tyr Arg Leu Leu Glu Xaa Ser Gln Asn Gln Gln Glu Lys
    130                 135                 140

Asn Glu Lys Asp Leu Leu Ala Leu Asp Ser Trp Xaa Asn Leu Trp Asn
145                 150                 155                 160

Trp Phe Xaa Ile Thr Asn
                165

<210> SEQ ID NO 21
<211> LENGTH: 166
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 101, 144
<223> OTHER INFORMATION: Xaa = Asp, Glu, His, Lys, or Arg
<220> FEATURE:
<221> NAME/KEY: VARIANT
<222> LOCATION: 104
<223> OTHER INFORMATION: Xaa = Ser or Thr
<220> FEATURE:
<221> NAME/KEY: VARIANT
<222> LOCATION: 106, 110, 125
<223> OTHER INFORMATION: Xaa = Ala, Cys, Asp, Gly, Asn, Pro, Ser, Thr,
      or Val
<220> FEATURE:
<221> NAME/KEY: VARIANT
<222> LOCATION: 107, 108
<223> OTHER INFORMATION: Xaa = any amino acid

<400> SEQUENCE: 21

Ala Val Gly Leu Gly Met Leu Phe Leu Gly Val Leu Ser Ala Ala Gly
 1               5                  10                  15

Ser Thr Met Gly Ala Ala Ala Thr Ala Leu Thr Val Gln Thr His Thr
             20                  25                  30

Leu Met Lys Gly Ile Val Gln Gln Gln Asp Asn Leu Leu Arg Ala Ile
         35                  40                  45

Gln Ala Gln Gln Gln Leu Leu Arg Leu Ser Val Trp Gly Ile Arg Gln
 50                  55                  60
```

```
Leu Arg Ala Arg Leu Leu Ala Leu Glu Thr Leu Ile Gln Asn Gln Gln
 65                  70                  75                  80

Leu Leu Asn Leu Trp Gly Cys Lys Gly Arg Leu Ile Cys Tyr Thr Ser
                 85                  90                  95

Val Lys Trp Asn Xaa Thr Trp Xaa Gly Xaa Xaa Xaa Asp Xaa Ile Trp
             100                 105                 110

Gly Asn Leu Thr Trp Gln Glu Trp Asp Gln Gln Ile Xaa Asn Ile Ser
             115                 120                 125

Ser Ile Ile Tyr Asp Glu Ile Gln Lys Ala Gln Val Gln Gln Glu Xaa
             130                 135                 140

Asn Glu Lys Lys Leu Leu Glu Leu Asp Glu Trp Ala Ser Ile Trp Asn
145                 150                 155                 160

Trp Leu Asp Ile Thr Lys
                165

<210> SEQ ID NO 22
<211> LENGTH: 166
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 96, 113, 125, 129, 133
<223> OTHER INFORMATION: Xaa = Ala, Cys, Asp, Gly, Asn, Pro, Ser, Thr,
      or Val
<220> FEATURE:
<221> NAME/KEY: VARIANT
<222> LOCATION: 101
<223> OTHER INFORMATION: Xaa = Ser or Thr
<220> FEATURE:
<221> NAME/KEY: VARIANT
<222> LOCATION: 109, 110
<223> OTHER INFORMATION: Xaa = Asp or Glu

<400> SEQUENCE: 22

Ala Val Gly Ile Gly Ala Ile Phe Leu Gly Phe Leu Gly Ala Ala Gly
  1               5                  10                  15

Ser Thr Met Gly Ala Ala Ser Ile Thr Leu Thr Val Gln Ala Arg Gln
                 20                  25                  30

Leu Leu Ser Gly Ile Val Gln Gln Gln Asn Asn Leu Leu Arg Ala Ile
             35                  40                  45

Glu Ala Gln Gln His Leu Leu Gln Leu Thr Val Trp Gly Ile Lys Gln
 50                  55                  60

Leu Gln Ala Arg Val Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Xaa
                 85                  90                  95

Val Pro Trp Asn Xaa Ser Trp Ser Asn Lys Ser Leu Xaa Xaa Ile Trp
             100                 105                 110

Xaa Asn Met Thr Trp Met Glu Trp Glu Arg Glu Ile Xaa Asn Tyr Thr
             115                 120                 125

Xaa Ile Ile Tyr Xaa Leu Ile Glu Glu Ser Gln Asn Gln Gln Glu Lys
             130                 135                 140

Asn Glu Gln Glu Leu Leu Glu Leu Asp Lys Trp Ala Ser Leu Trp Asn
145                 150                 155                 160

Trp Phe Asp Ile Thr Asn
                165
```